US009341641B2

(12) United States Patent
Boehm et al.

(10) Patent No.: US 9,341,641 B2
(45) Date of Patent: May 17, 2016

(54) CARTRIDGE FOR DISPENSING A FLUID

(71) Applicant: Roche Diagnostics Operations, Inc., Indianapolis, IN (US)

(72) Inventors: Christoph Boehm, Viernheim (DE); Peter Kupser, Mannheim (DE); Norbert Oranth, Voerstetten (DE); Juergen Spinke, Lorsch (DE); Thorsten Brueckner, Schriesheim (DE); Timo Klein, Altdorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/530,862

(22) Filed: Nov. 3, 2014

(65) Prior Publication Data
US 2015/0140669 A1 May 21, 2015

Related U.S. Application Data

(63) Continuation of application No. PCT/EP2012/072733, filed on Nov. 15, 2012.

(30) Foreign Application Priority Data

May 8, 2012 (EP) .................... 12167108

(51) Int. Cl.
*G01N 35/10* (2006.01)
*G01N 35/00* (2006.01)
*B01L 3/02* (2006.01)
*B01L 3/00* (2006.01)
*A61M 5/168* (2006.01)
*G01F 11/02* (2006.01)
*A61M 5/142* (2006.01)

(52) U.S. Cl.
CPC .......... *G01N 35/1002* (2013.01); *B01L 3/0224* (2013.01); *G01F 11/021* (2013.01); *G01N 35/1016* (2013.01); *A61M 5/14216* (2013.01); *A61M 5/16809* (2013.01); *B01L 3/0217* (2013.01); *B01L 2200/0605* (2013.01); *B01L 2200/0684* (2013.01); *B01L 2300/0681* (2013.01); *B01L 2400/0478* (2013.01); *B01L 2400/0644* (2013.01); *Y10T 436/119163* (2015.01); *Y10T 436/2575* (2015.01)

(58) Field of Classification Search
CPC ... Y10T 436/13; Y10T 436/00; Y10T 436/11; Y10T 436/119163; Y10T 436/25; Y10T 436/2575; G01N 35/1002; G01N 35/1016; G01N 35/10; G01N 35/1009; B01L 3/0224; B01L 3/0217; B01L 3/021; B01L 3/02; B01L 3/00; G01F 11/021; G01F 11/02; G01F 11/00; A61M 5/16809; A61M 5/16804
USPC ........ 436/56, 54, 43, 180, 174; 422/509, 522, 422/521, 63, 67
See application file for complete search history.

(56) References Cited

U.S. PATENT DOCUMENTS

| 3,753,632 | A | 8/1973 | Mills |
| 5,441,173 | A | 8/1995 | Koval et al. |
| 7,955,392 | B2 | 6/2011 | Haueter et al. |
| 2009/0176314 | A1 | 7/2009 | Steinboeck et al. |

FOREIGN PATENT DOCUMENTS

| EP | 1987890 A1 | 11/2008 | |
| WO | WO 2006/048643 | * 5/2006 | ............. G01N 35/10 |

OTHER PUBLICATIONS

International Search Report issued May 23, 2013 in Application No. PCT/EP2012/072733, 3 pages.
Cartridge—Definition and More from the Free Merriam-Webster Dictionary, retrieved May 13, 2014, 2 pages.

* cited by examiner

*Primary Examiner* — Christine T Mui
(74) *Attorney, Agent, or Firm* — Roche Diagnostics Operations, Inc.

(57) ABSTRACT

A cartridge for dispensing fluid is presented. The cartridge comprises a valve. The valve comprises a pumping chamber for pumping the fluid. The valve positions a pumping chamber conduit. The pumping chamber conduit is connected to the pumping chamber. The cartridge further comprises a plunger for changing the volume of the pumping chamber. The cartridge further comprises a reservoir conduit for connecting the reservoir with the valve. The valve positions the pumping chamber conduit to connect with the reservoir conduit. The cartridge further comprises an outlet conduit for dispensing the fluid. The valve further rotates the pumping chamber conduit to connect with the outlet conduit.

20 Claims, 30 Drawing Sheets

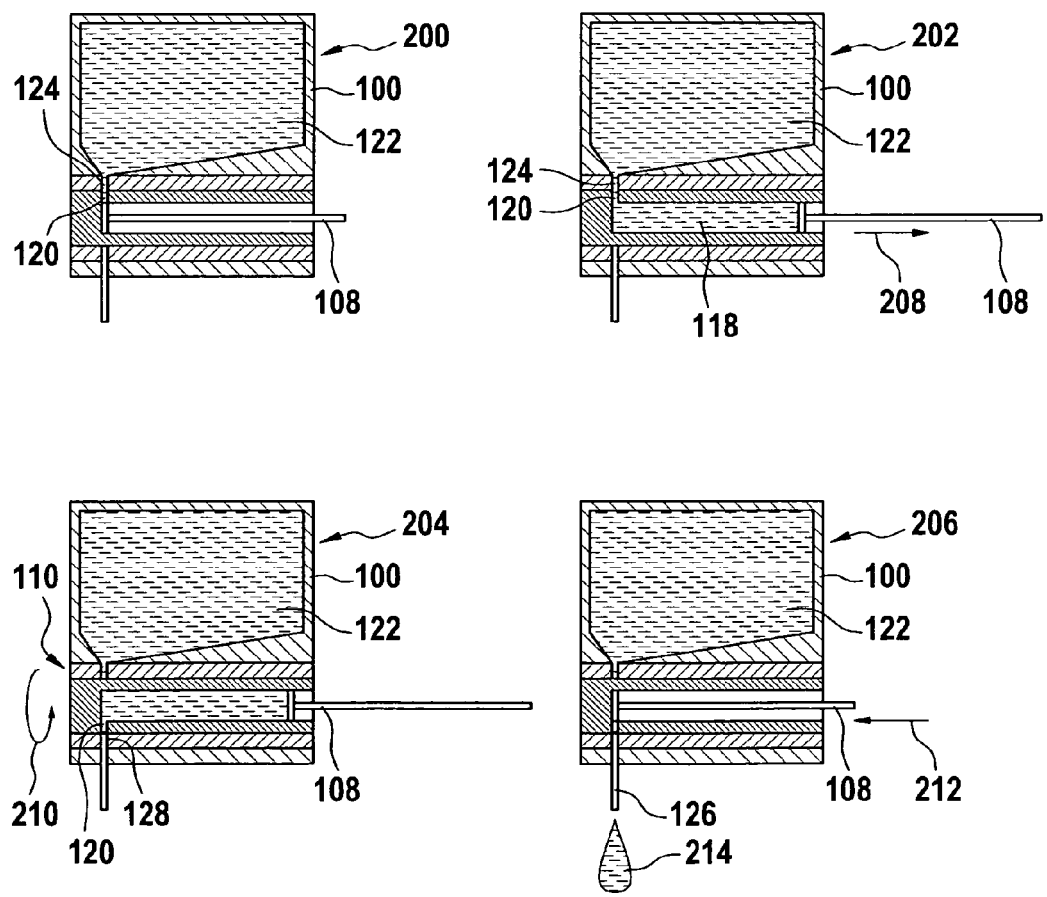

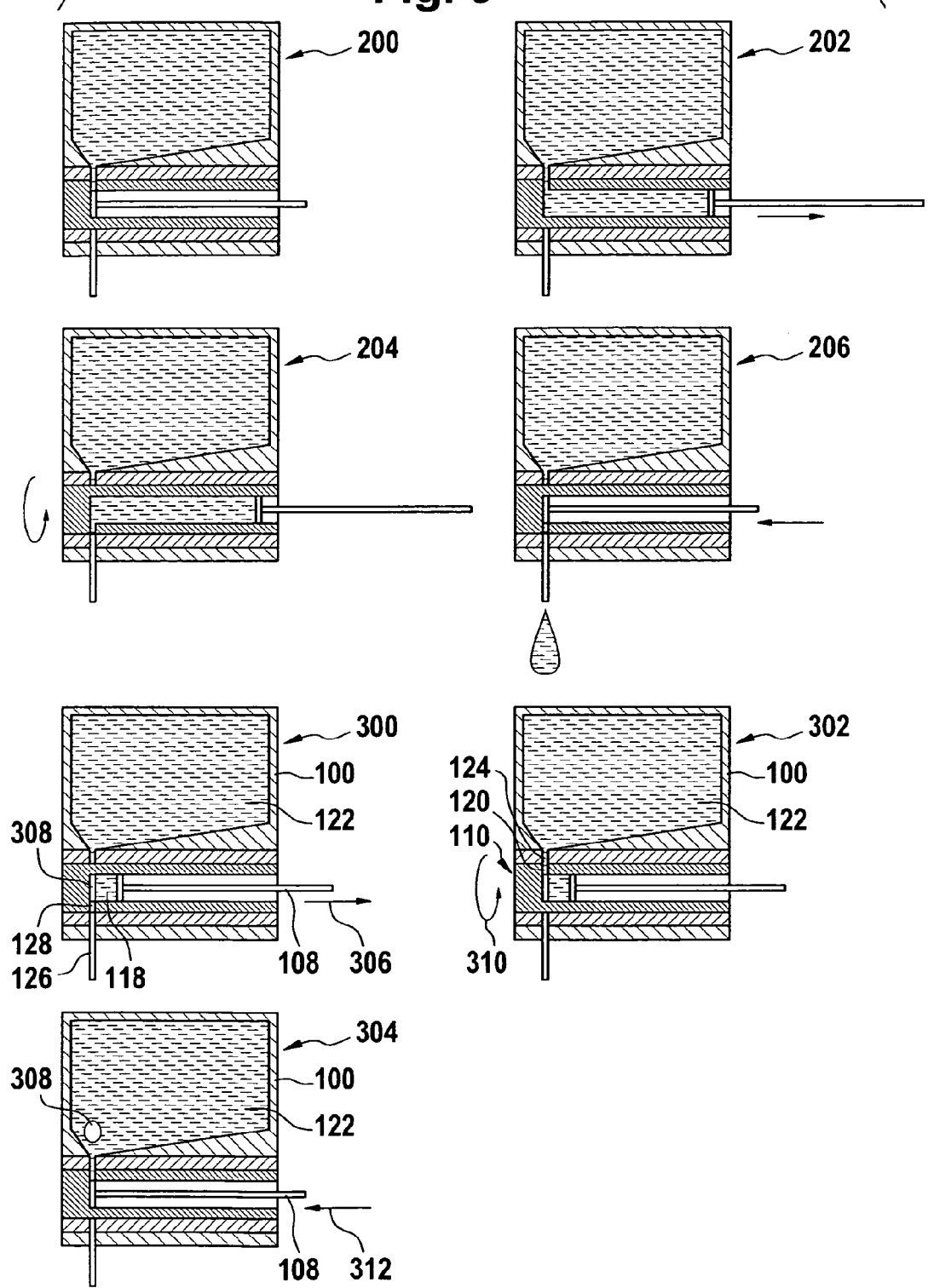

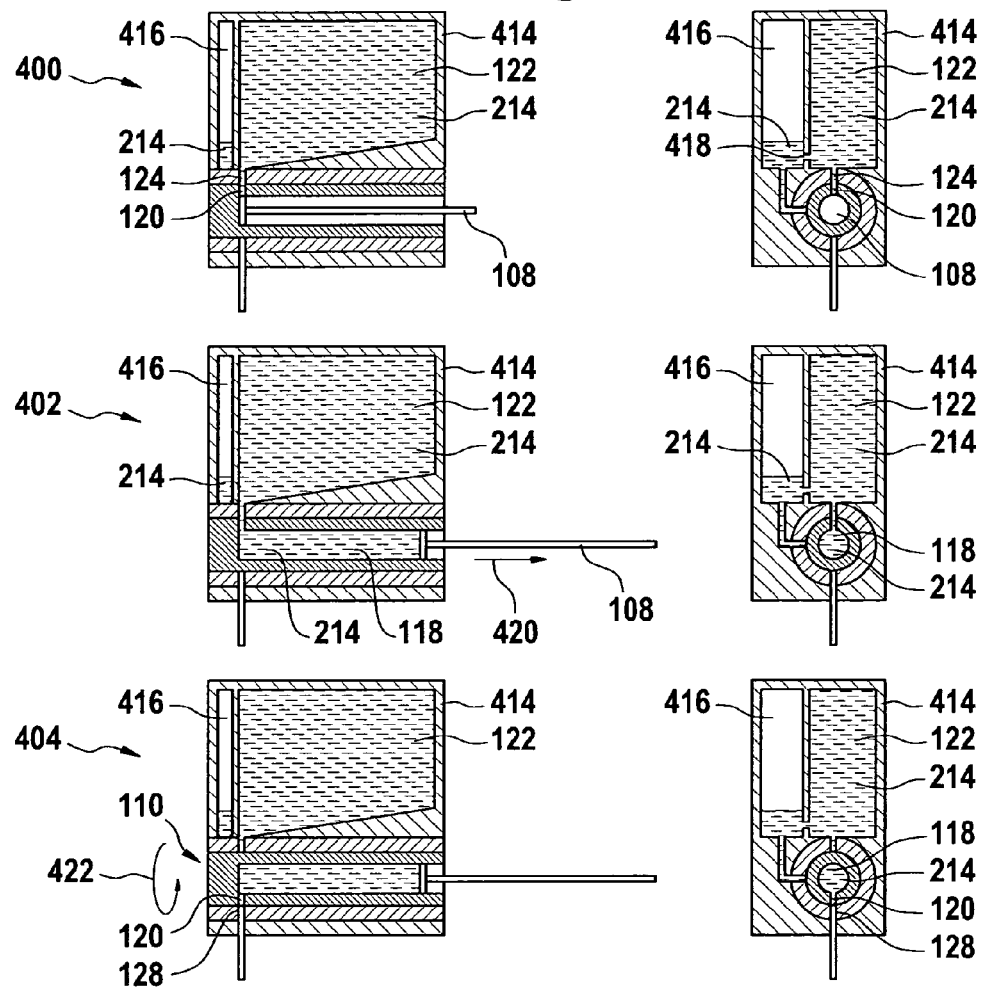

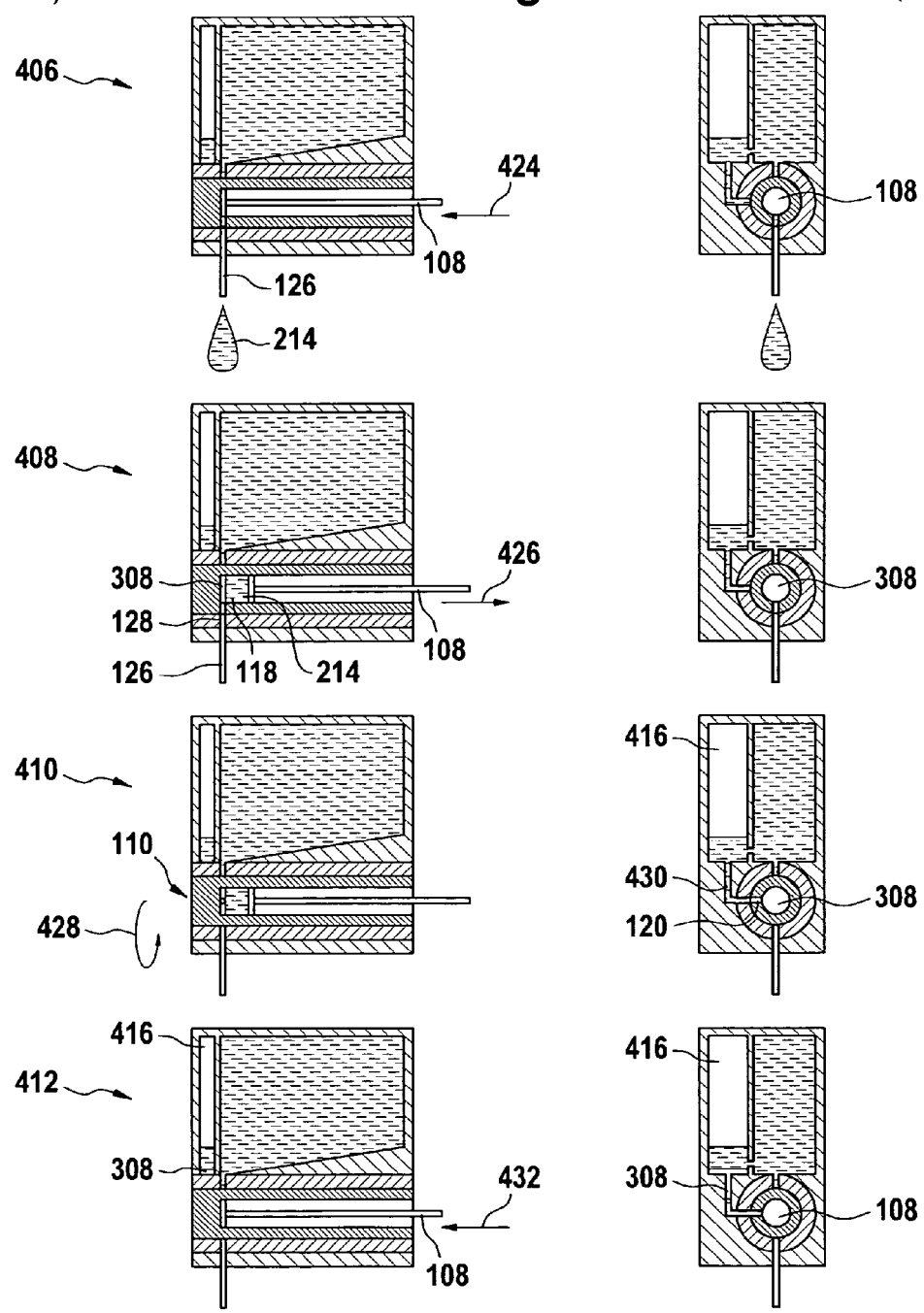

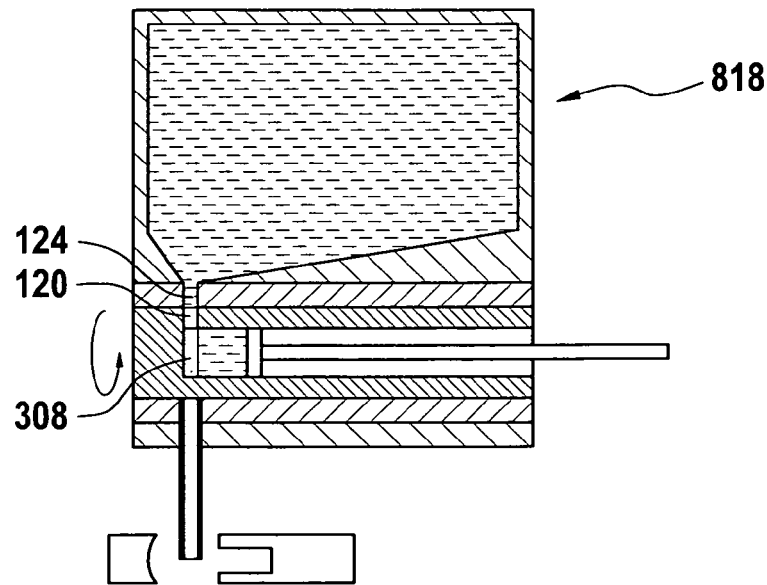
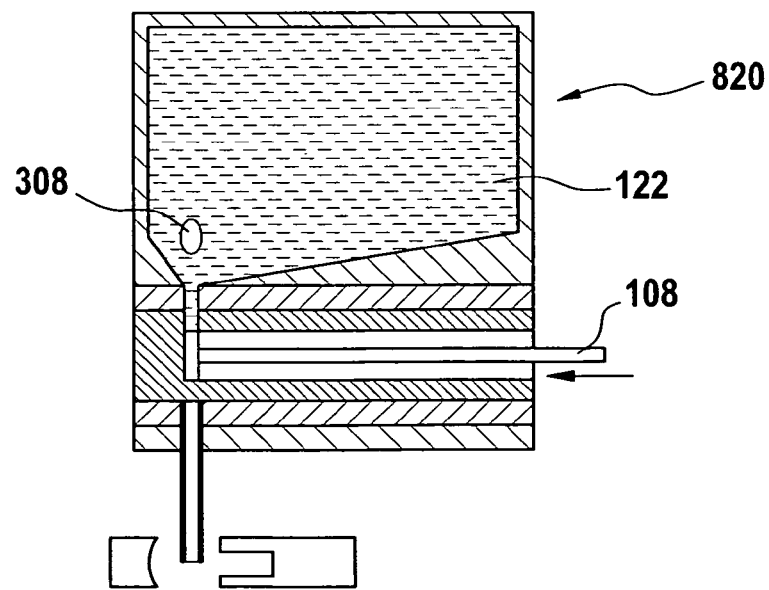
Fig. 8D

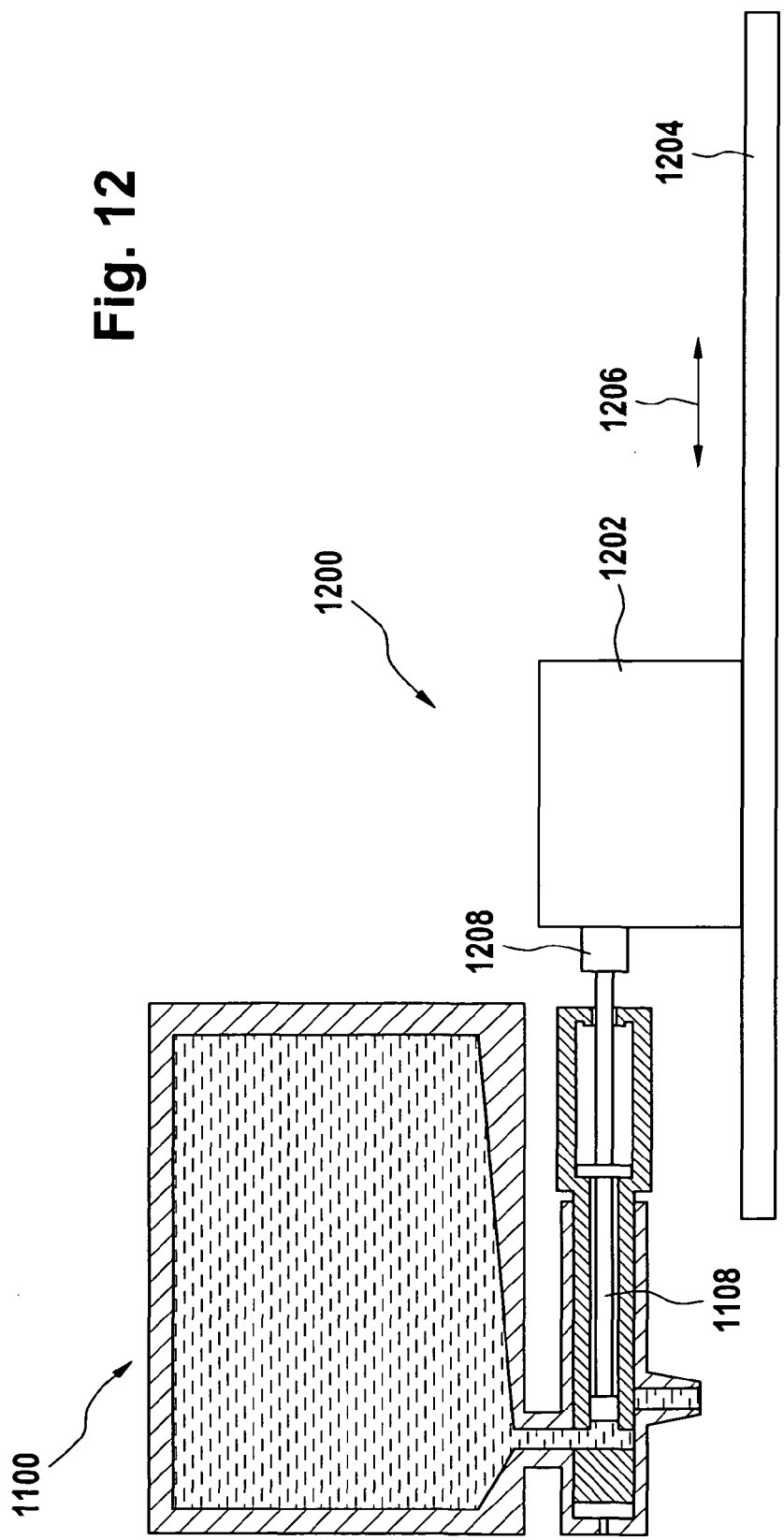

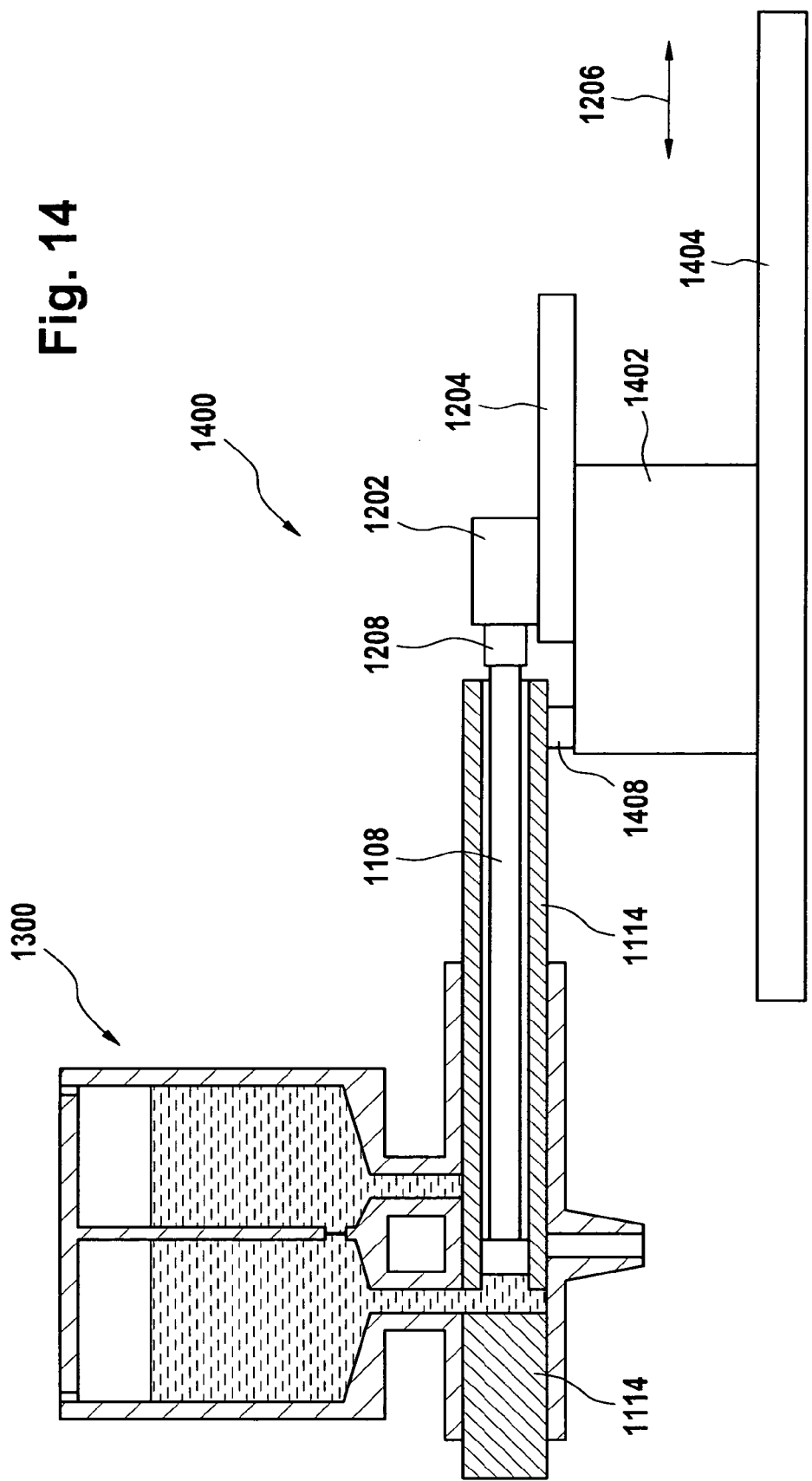

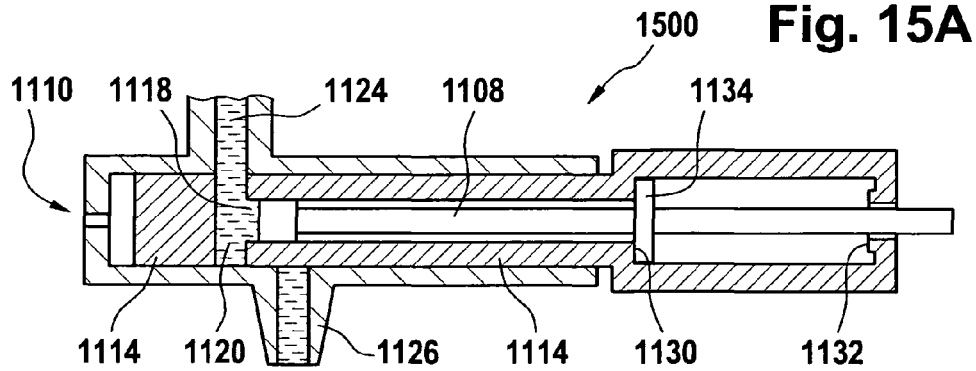
Fig. 15A
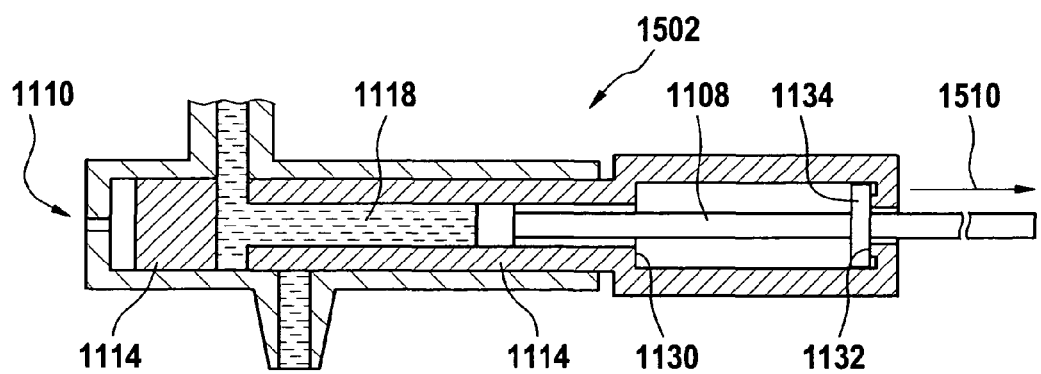
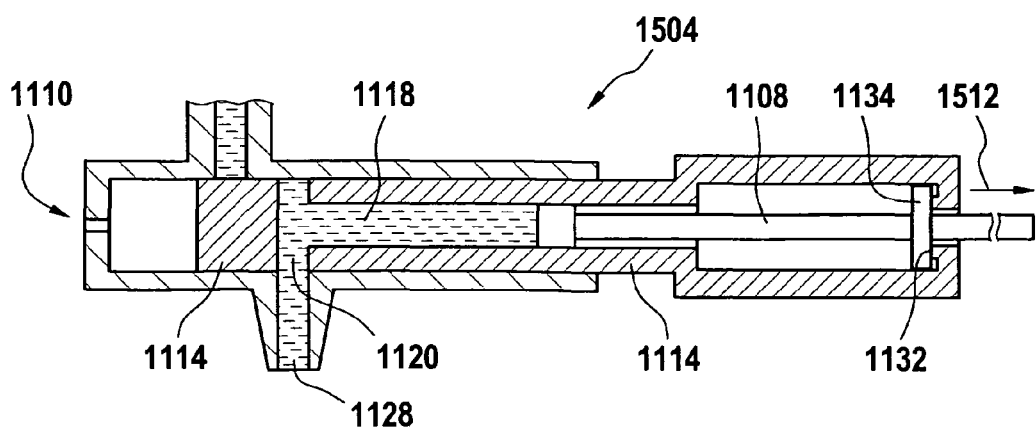

Fig. 15B
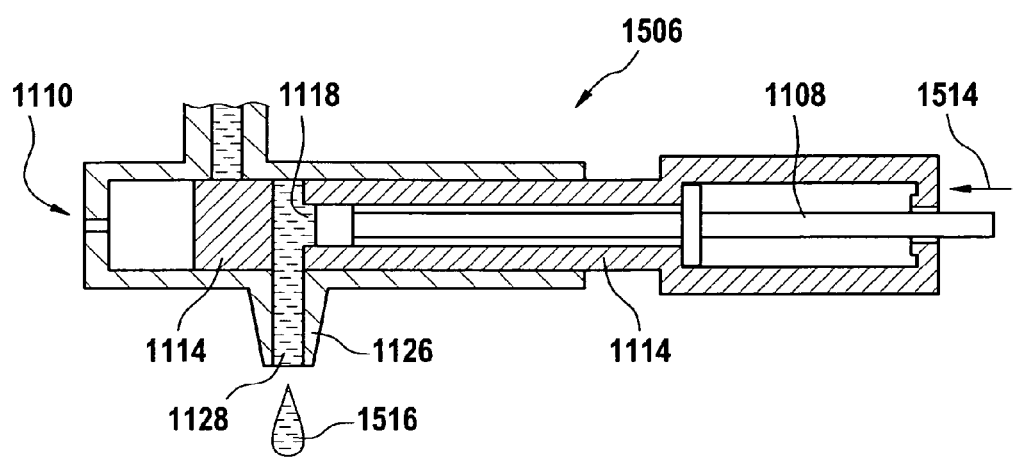
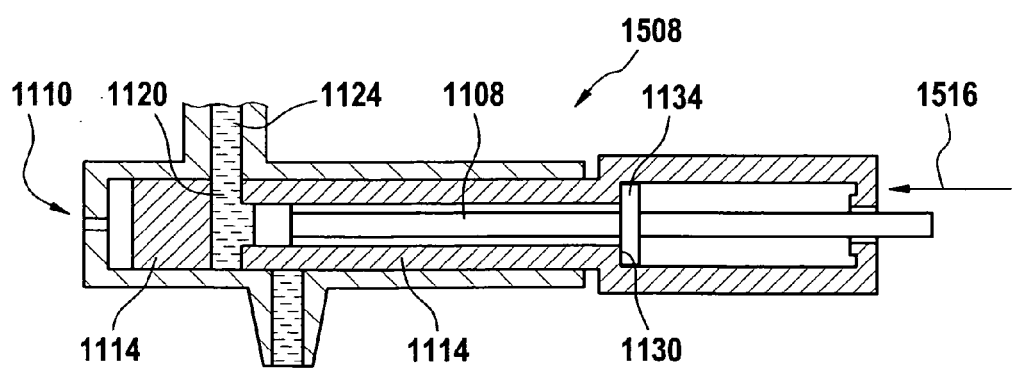

Fig. 16A
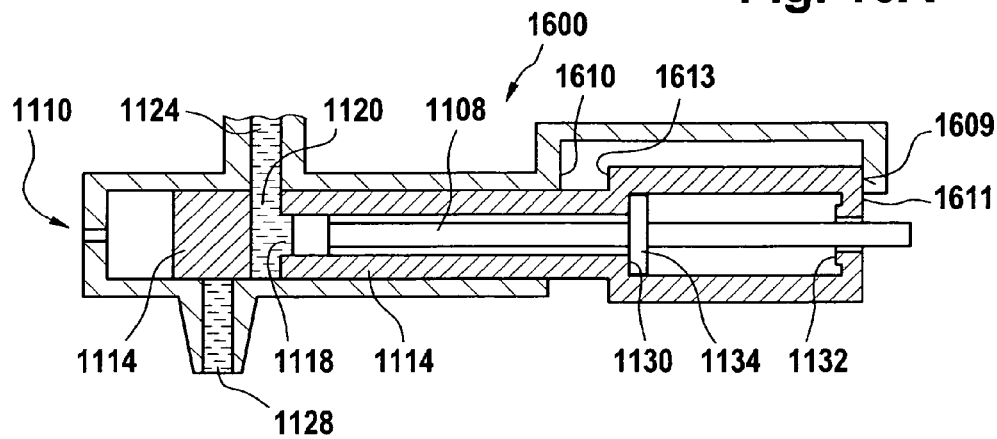
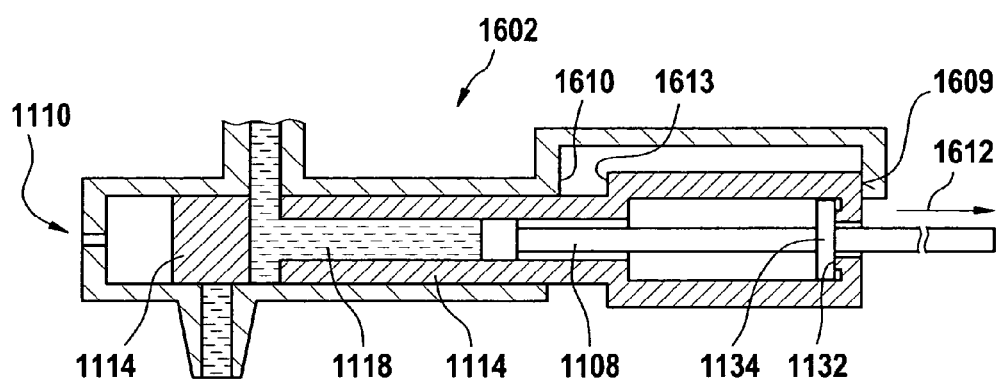
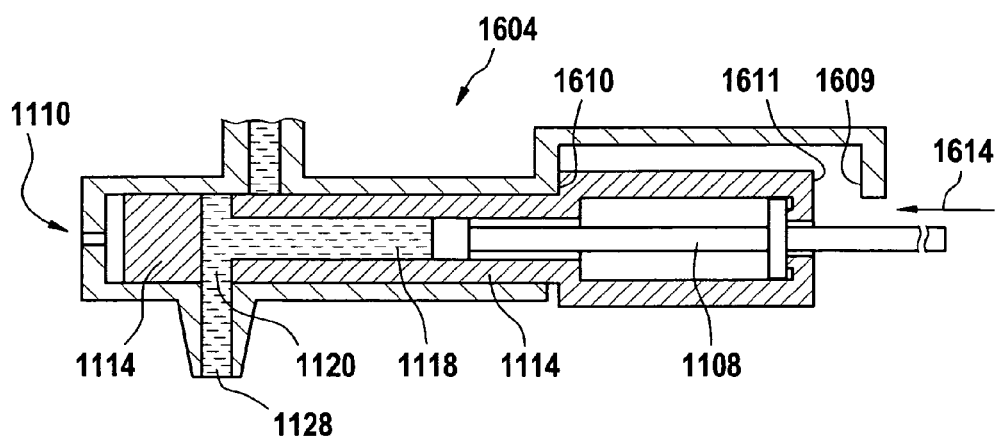

Fig. 16B
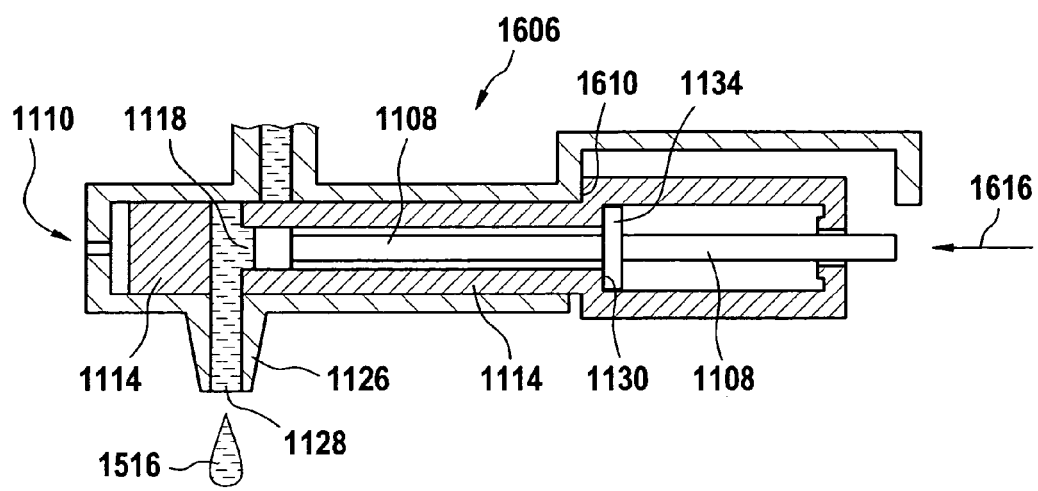
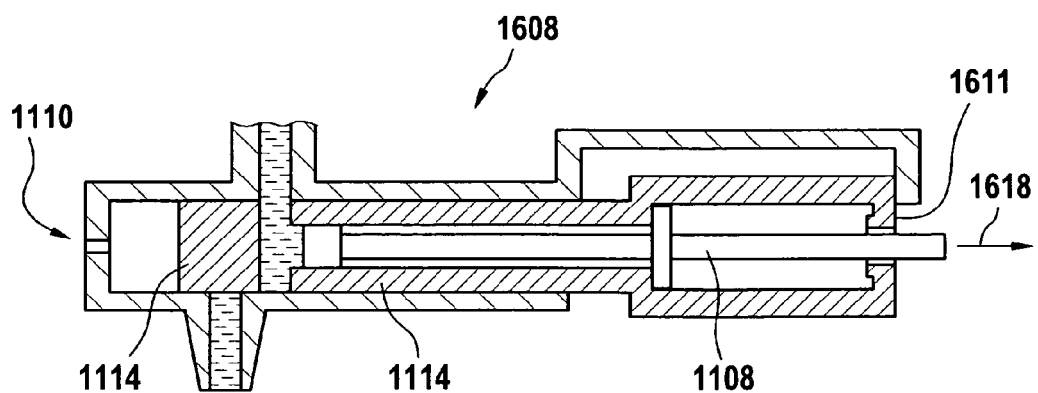

Fig. 17
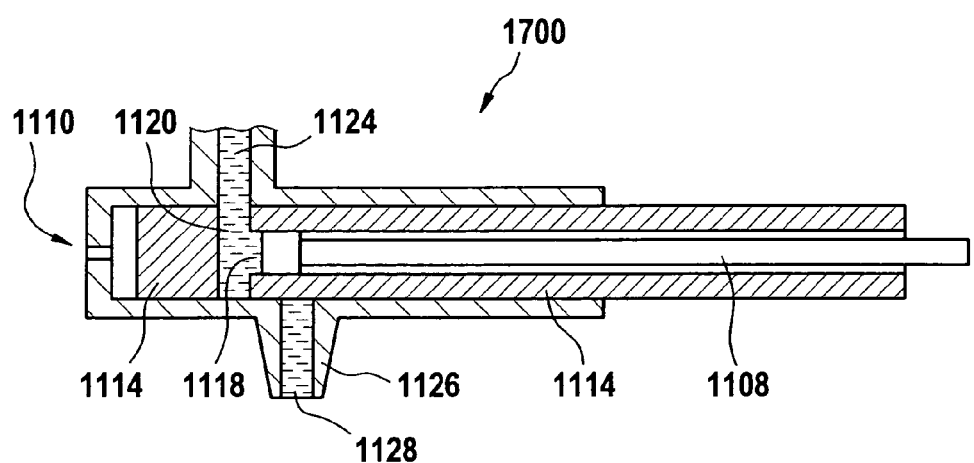
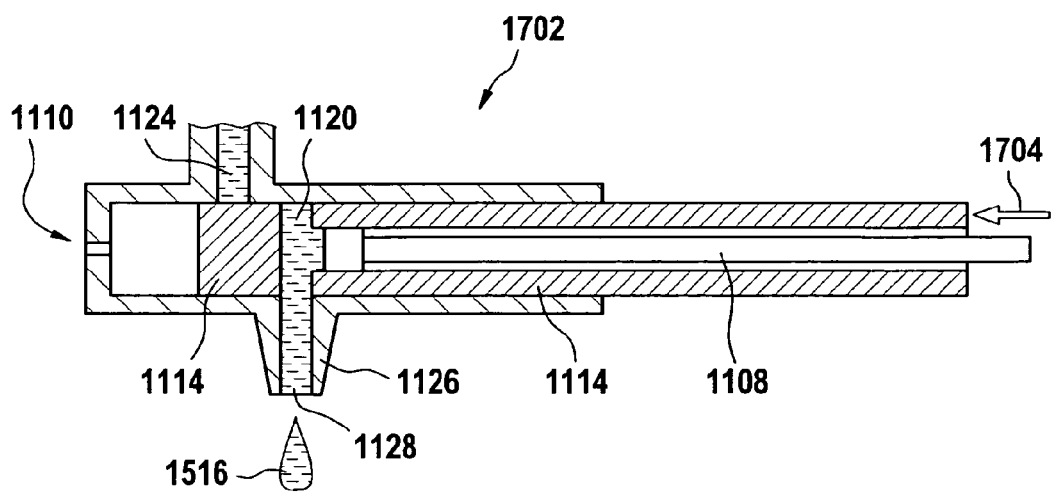

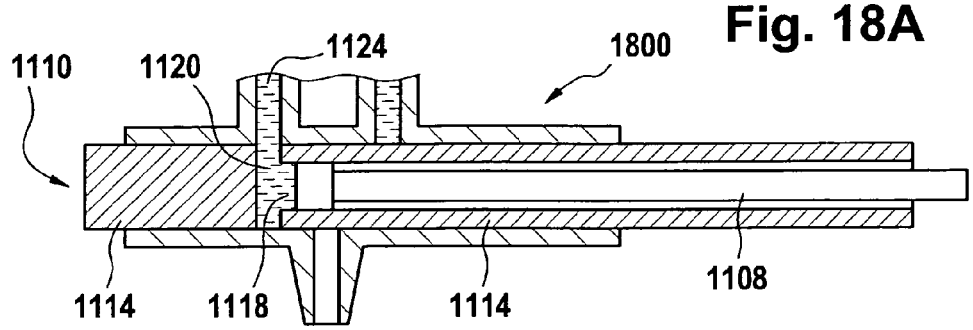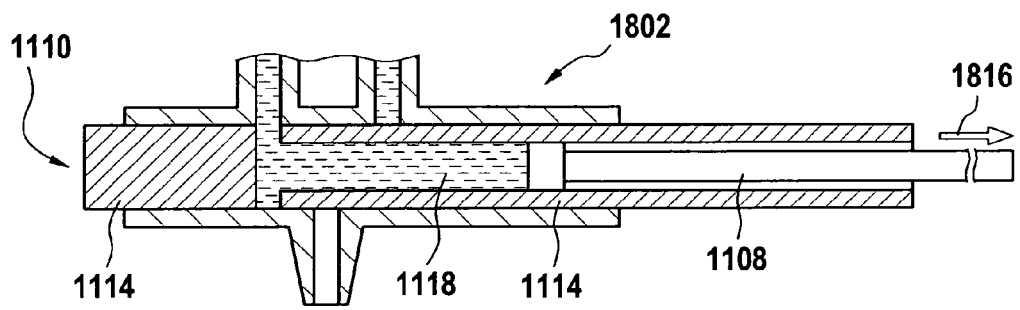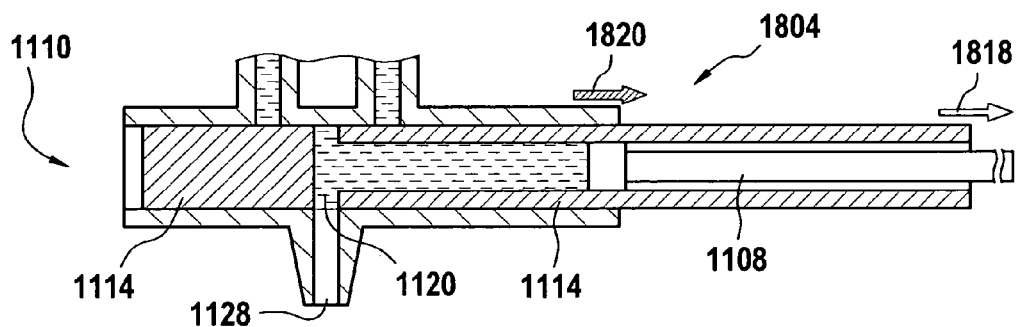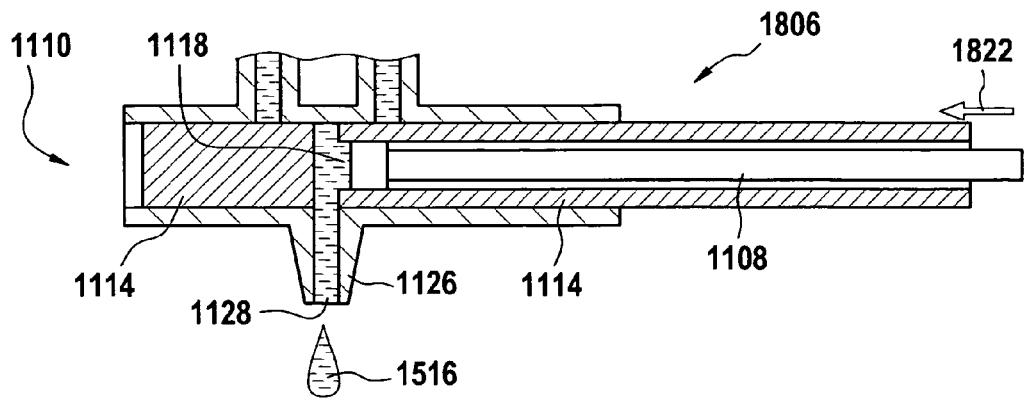
Fig. 18A

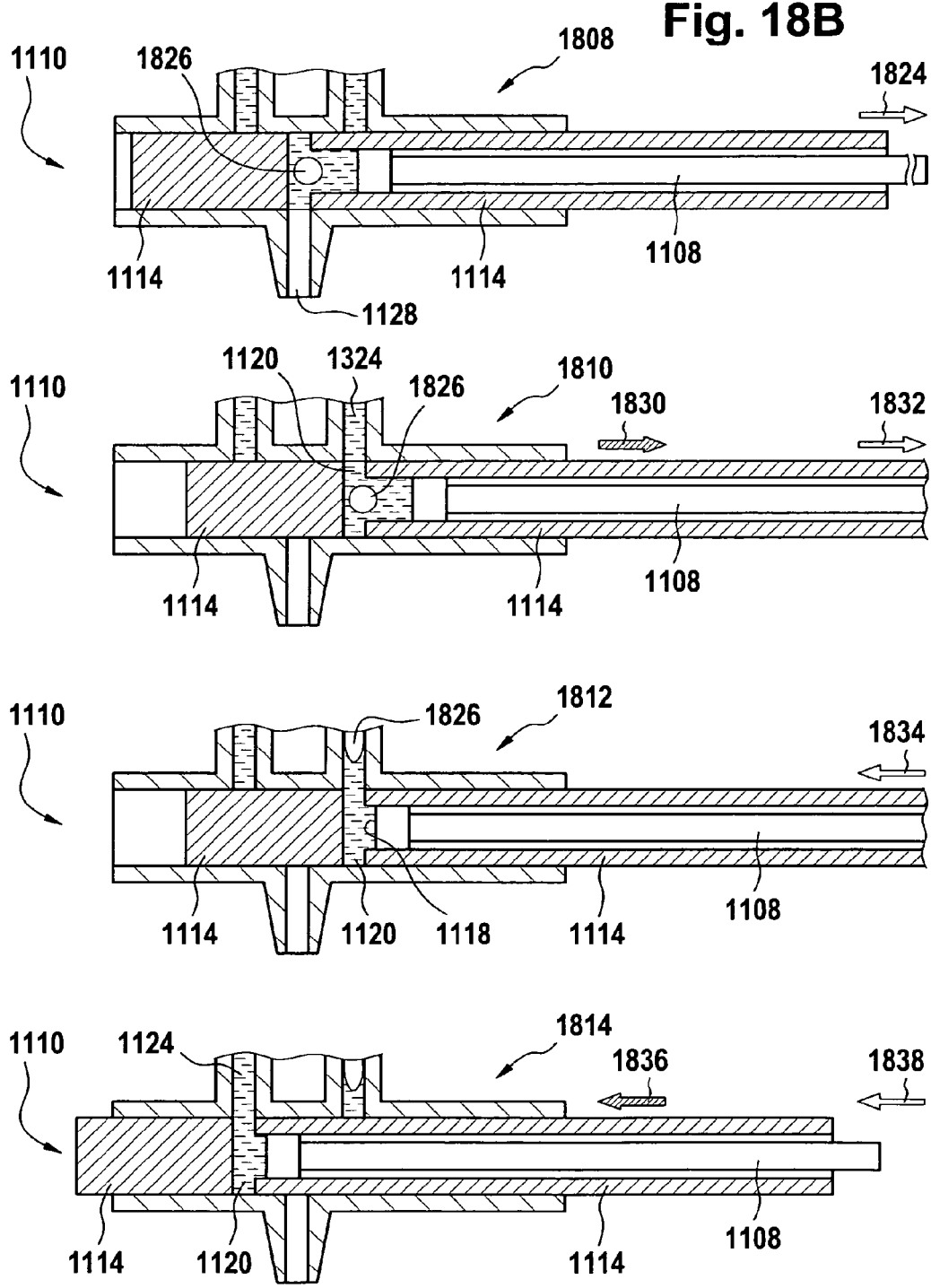

CARTRIDGE FOR DISPENSING A FLUID

CROSS-REFERENCE TO RELATED APPLICATIONS

This application is a continuation of PCT/EP2012/072733, filed Nov. 15, 2012, which is based on and claims priority to EP 12167108.5, filed May 8, 2012, which is hereby incorporated by reference.

BACKGROUND

The present disclosure generally relates to cartridges for dispensing a fluid and an automatic analyzer for dispensing the fluid using the cartridge.

In medical laboratories, in vitro diagnostics are commonly performed on biological samples such as blood, urine, blood plasma and saliva. Such tests may be performed manually using pipettes or maybe performed using an automatic analyzer. Automatic analyzers may automatically add reagents to the biological sample and may measure one or more parameters of the biological sample during analysis.

SUMMARY

According to the present disclosure, a cartridge for dispensing fluid is presented. The cartridge can comprise a valve. The valve can comprise a pumping chamber for pumping the fluid. The valve can position a pumping chamber conduit. The pumping chamber conduit can be connected with the pumping chamber. The cartridge can further comprise a plunger for changing the volume of the pumping chamber and a reservoir conduit for connecting the reservoir with the valve. The valve can position the pumping chamber conduit to connect with the reservoir conduit. Finally, the cartridge can comprise an outlet conduit for dispensing the fluid. The valve can rotate the pumping chamber conduit to connect with the outlet conduit.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 2 illustrates how the cartridge may be used to pump fluid through the outlet conduit according to an embodiment of the present disclosure.

FIG. 3 illustrates a pumping method similar to that shown in FIG. 2 except additional steps are performed to remove fluid from the outlet conduit according to an embodiment of the present disclosure.

FIGS. 4A-B illustrate how fluid can be pumped through the outlet conduit where the fluid is taken from the reservoir and then excess fluid from the outlet nozzle and outlet conduit is pumped into the secondary reservoir according to an embodiment of the present disclosure.

FIGS. 8A-D illustrate the operation of a cartridge using a meniscus detector according to an embodiment of the present disclosure.

FIG. 12 illustrates the cartridge of FIG. 1 connected to an actuator assembly according to an embodiment of the present disclosure.

FIG. 14 illustrates the cartridge of FIG. 2 connected to an actuator assembly according to an embodiment of the present disclosure.

FIGS. 15A-B illustrate views on different phases of the slide valve and plunger of the embodiment shown in FIG. 1 according to an embodiment of the present disclosure.

FIG. 16A-B illustrate a slide valve and a piston combination according to an embodiment of the present disclosure.

FIG. 17 illustrates two views of a slide valve and plunger combination according to another embodiment of the present disclosure.

FIGS. 18A-B illustrate one way of operating the slide valve and piston of the embodiment shown in FIG. 3 according to an embodiment of the present disclosure.

DETAILED DESCRIPTION

Figure 1:
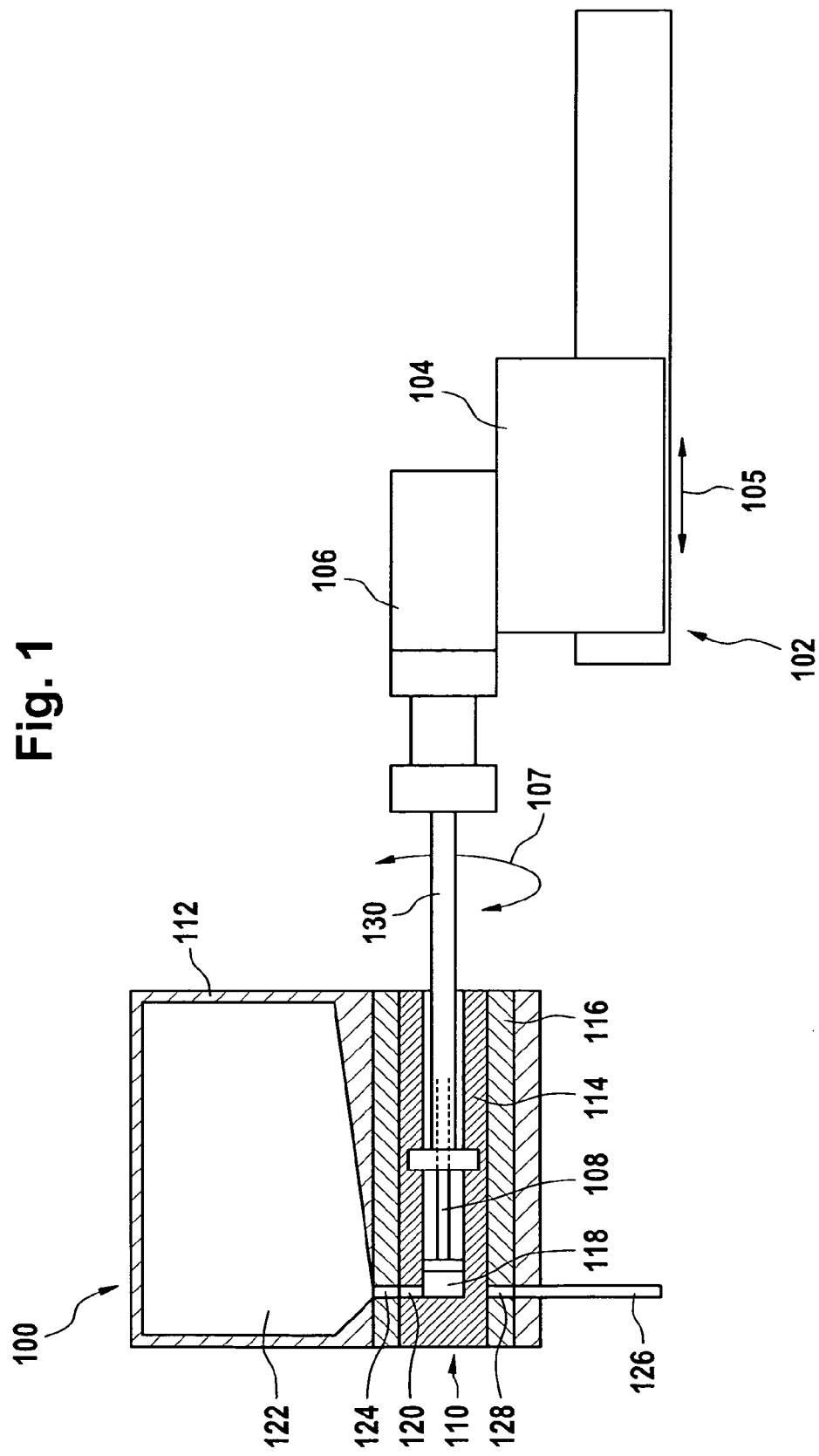
FIG. 1 illustrates a cartridge and an actuator assembly according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A cartridge for dispensing a fluid is presented. In some embodiments, the cartridge can comprise a rotary valve which may be moved in a circular fashion to position a pumping chamber conduit coming from a pumping chamber. Rotation of the rotary valve can enable the pumping chamber conduit to be connected to one of a variety of other conduits. The pumping chamber can be formed by a cavity within the rotary valve and by a plunger which can change the volume of the pumping chamber. In other embodiments, a linear valve can be used for positioning the pumping chamber conduit.

The cartridge can comprise a reservoir for storing the fluid and an outlet conduit for dispensing a fluid. A reservoir conduit can connect the reservoir with the valve. In some embodiments, the outlet conduct conduit can connect an outlet nozzle to the valve. As the valve is moved in different positions, the pumping chamber conduit can be positioned at either the reservoir conduit or the outlet conduit. In some embodiments, the valve and the plunger may be able to be operated or actuated independently of each other. Embodiments of this cartridge may have the advantage that they can be operated such that the cartridge does not lose any fluid or that the fluid loss due to priming can be reduced.

A controller as used herein can encompass a device, machine, or apparatus for controlling the operation and/or function of one or more other devices. Examples of a controller may include, but are not limited to: a computer, a processor, an imbedded system or controller, a programmable logic controller, and a microcontroller. A 'computing device' or 'computer' as used herein can encompass any device comprising a processor. A 'processor' as used herein can encompass an electronic component which can be able to execute a program or machine executable instruction.

A 'computer-readable storage medium' as used herein can encompass any tangible storage medium which may store instructions which can be executable by a processor of a computing device. The computer-readable storage medium may be referred to as a computer-readable non-transitory storage medium.

'Computer memory' or 'memory' can be examples of a computer-readable storage medium. Computer memory can be any memory which can be directly accessible to a processor or other controller. 'Computer storage' or 'storage' can be examples of a computer-readable storage medium. Computer storage can be any non-volatile computer-readable storage medium.

A 'user interface' as used herein can be an interface which can allow a user or operator to interact with a computer or computer system.

A 'hardware interface' as used herein can encompass an interface which can enable a processor or other controller to interact with and/or control an external computing device and/or apparatus. A hardware interface may allow a processor to send control signals or instructions to an external computing device and/or apparatus. The hardware interface may enable the processor or other controller to receive sensor data and control the dispensing of the fluid. The hardware interface may be used to form a closed control loop in some embodiments.

A cartridge for dispensing fluid is provided. The cartridge can comprise a valve. The valve can comprise a pumping chamber for pumping the fluid. The valve can position a pumping chamber conduit. The pumping chamber conduit can be connected with the pumping chamber. The valve further can comprise a plunger for changing the volume of the pumping chamber. The valve can further comprise reservoir conduit for connecting the reservoir with the valve. The valve can position the pumping chamber conduit to connect with the reservoir conduit. The valve can further comprise an outlet conduit for dispensing the fluid. The valve can rotate the pumping chamber conduit to connect with the outlet conduit.

A cartridge for dispensing fluid is provided. The cartridge can comprise a rotary valve. The rotary valve can comprise a pumping chamber for pumping the fluid. The rotary valve can rotate a pumping chamber conduit. The pumping chamber conduit can be connected with the pumping chamber. In other words, there can be a rotary valve which can have a pumping chamber conduit connected to a pumping chamber within it. By rotating the rotary valve, the pumping chamber conduit can be rotated into different positions thereby allowing the pumping chamber to be connected to other conduits.

The cartridge can further comprise a plunger for changing the volume of the pumping chamber. The rotary valve and the plunger can be actuated independently. In other words, the plunger and the rotary valve can be able to be operated such that the plunger can be used to change the volume of the pumping chamber without affecting the position of the rotary valve and vice versa. This may enable a larger set of pumping actions by the pumping chamber.

The cartridge can further comprise a reservoir for storing the fluid. The reservoir can be constructed in a variety of ways. In some embodiments, the reservoir may be a hard walled chamber and, in one embodiment, can be made of plastics using injection moulding or thermoforming processes. In some embodiments, the reservoir may be a chamber with a flexible wall. In some embodiments, the reservoir could be a pouch or bladder. In other embodiments, the reservoir can be a pouch or bladder supported by an outer container. In other embodiments, the reservoir can be a tube.

The cartridge can further comprise a reservoir conduit for connecting the reservoir with the rotary valve. The rotary valve can rotate the pumping chamber conduit to connect with the reservoir conduit. When the pumping chamber conduit is rotated into the correct position, then there can be communication between the pumping chamber and the reservoir.

The cartridge can further comprise an outlet conduit for dispensing the fluid and for connecting to the rotary valve. The rotary valve can further rotate the pumping chamber conduit to connect to the outlet conduit. This embodiment may have the advantage that a large variety of pumping actions can be performed with the pumping chamber by controlling the rotational position of the rotary valve and properly operating the plunger. For instance, the rotary valve may be positioned such that the pumping chamber conduit can be connected to the reservoir conduit. In this case, the plunger may be used to either withdraw fluid from the reservoir into the pumping chamber or may be used to pump the fluid from the pumping chamber back into the reservoir.

This embodiment may enable other types of actions using the pumping chamber. For instance, when the pumping chamber conduit is aligned or connected with the reservoir conduit, the plunger may be repeatedly used to increase and decrease the volume of the pumping chamber. This may enable the fluid within the reservoir to be mixed. Also the ability to put the fluid back into the reservoir may reduce the amount of fluid that may be wasted.

This embodiment may also enable a so-called reduced waste priming or non-waste priming function of the pumping chamber whereby none or possibly only a very small amount of the fluid may be wasted or discarded when fluid is pumped out through the outlet conduit. For instance, when the pumping chamber conduit is connected with the outlet conduit, the plunger may be used to decrease the volume of the pumping chamber and thereby force or dispense fluid out through the outlet conduit. During the process of doing this, there may be fluid within the outlet conduit which may not exit the outlet conduit. After the correct amount of fluid has been dispensed, the plunger may then be used to increase the volume of the pumping chamber thereby withdrawing fluid that may remain within the outlet conduit back into the pumping chamber. Fluid can then be held within the pumping chamber or if the rotary valve is rotated into alignment with the reservoir conduit the fluid which was previously within the outlet conduit may be pumped back into the reservoir.

The rotary valve may also prevent fluid from accidentally leaking from the reservoir. For instance, the rotary valve may be able to be rotated in some embodiments to a position where it is neither aligned with the outlet conduit nor with the reservoir conduit. This may prevent fluid and/or gas from exiting from the outlet conduit and/or from fluid and/or gas in a reservoir leaking or draining into the pumping chamber.

In another embodiment, the cartridge can further comprise an outlet nozzle connected to the outlet conduit. An outlet nozzle as used herein can encompass a nozzle design to minimize the waste of fluid and may enable drops to cleanly drip during the dosing process. For instance, in a simple tube, a drop of the fluid may hang outside the nozzle after the plunger is used to decrease the volume of the pumping chamber. The shape or function of the outlet nozzle can be designed to reduce the chances of a drop of the fluid hanging on it. For instance, the outlet nozzle may have a so-called duckbill shape and be a duckbill nozzle.

In other embodiments, the cartridge may have additional reservoirs and additional reservoir conduits which can enable the pumping chamber to be connected to these additional reservoirs. Typically, a cartridge may contain only a single fluid or reagent. In some embodiments, this may be a diluent that can be used or required for various tests. There may also be multiple reservoirs which may be each connected to a conduit accessible to the pumping chamber conduit at a particular rotational position of the rotary valve.

For example, for many clinical tests, there may be two reservoirs and, for immunoassays, there may be two or three different fluids within different reservoirs. In some embodiments, the cartridge may have multiple pumping units, with each of the pumping units connected to one or more reservoirs via its rotary valve. In this way, the immunoassays can be dispensed using separate pumping units and they may not be mixed by the pumping process.

In another embodiment, the cartridge can further comprise a return conduit connected to the reservoir. The pumping chamber conduit can receive fluid from a first portion of the reservoir. The return conduit can return fluid to a second portion of the reservoir. The rotary valve can further rotate the pumping chamber conduit to connect to the return conduit. This embodiment may be beneficial because it may, for instance, reduce the effect of potentially occurring gas bubbles when fluid is returned to the reservoir. This embodiment may further have the benefit of reducing the number of bubbles within the first portion of the reservoir by transmitting the bubbles to the second portion of the reservoir.

For instance, fluid can be drawn from the reservoir when the rotary valve can be rotated such that the pumping chamber conduit can be in alignment with the reservoir conduit. After a certain amount of the fluid has been dispensed through the outlet conduit, the rotary valve may be rotated into such a position such that the pumping chamber conduit can be in alignment with the return conduit. The reservoir conduit may draw fluid from one portion of the reservoir and the return conduit can be used to return the fluid to a different portion of the reservoir. For instance, the two locations of the reservoir conduit and the return conduit can be far enough away that it may be unlikely that bubbles which enter the reservoir through the return conduit can be drawn into the reservoir conduit when fluid can be drawn from the reservoir into the pumping chamber.

In another embodiment, the cartridge can further comprise a secondary reservoir. The cartridge can further comprise a secondary reservoir conduit. The rotary valve can further rotate the pumping chamber conduit to connect to the secondary reservoir conduit. This embodiment may be beneficial because it may enable a second or distinct fluid to be stored and dispensed using the cartridge, it may also enable waste fluid to be disposed of in the secondary reservoir.

It should be noted that additional reservoirs may be added to the cartridge by adding a third reservoir and a third reservoir conduit, a fourth reservoir and a fourth reservoir conduit, and so on so that any number of reservoirs and reservoir conduits may be added to the cartridge.

In another embodiment, the cartridge can further comprise a connecting conduit. The connecting conduit can transport fluid between the secondary reservoir and the reservoir. This embodiment may be beneficial because the connecting conduit may enable the secondary reservoir to be used as a place to deposit fluid in order to return it to the reservoir.

In another embodiment, the cartridge can comprise a membrane blocking the connecting conduit. The membrane can be permeable to the fluid. This embodiment may be beneficial because it may provide a filtering fluid or blocking of gas bubbles when fluid is returning from the secondary reservoir into the reservoir.

In another embodiment, the secondary reservoir can comprise a bubble guiding structure. A bubble guiding structure as used herein can encompass a structure which can be used to guide a gas bubble to a predetermined location in a reservoir or towards a vent. In some implementations, the bubble guiding structure may allow fluid to pass around the bubble as it is moving through the reservoir. For instance, a bubble structure may be a set of ridges which can be used to position and guide a bubble. The structures and ridges may be spaced close enough together such that the surface tension of the fluid can prevent the bubble from going into regions which can allow the fluid to go around the bubble. This may be beneficial because if the bubble is not properly confined, the bubble may get stuck at a particular position in the secondary reservoir and not allowed to go to the top of the secondary reservoir or in the case where there is a connecting conduit to allow the fluid to return to the reservoir.

In another embodiment, the reservoir and/or the secondary reservoir can comprise a vent. A vent as used herein can be a structure which can enable air bubbles or other gas volumes to enter or leave the cartridge. Alternatively, the reservoir can comprise such a vent or both the reservoir and the second reservoir can comprise such vents In another embodiment, the vent can be covered or sealed with a filter. The filter can seal the fluid in the cartridge. The filter may be hydrophobic in some embodiments. In some embodiments, the gas filter may have micropores to only let gas through, but no liquids. In some embodiments, the filter may be, but is not limited to: a porous form of polytetrafluoroethylene, carbon fibers, carbon fibers coated with PTFE, carbon nanotubes, polymer fibers, or fluoropolymer fibers In another embodiment, the fluid can comprise magnetic beads, latex beads, a blood grouping reagent, an immune reagent, an antibody, an enzyme, a recombinant protein, a virus isolate, a virus, a biological reagent, a solvent, a diluent, a dispersion, nanoparticles, a protein, a salt, a detergent, a nucleic acid, an acid, a base or combinations thereof.

In another embodiment, the fluid may comprise a particles suspension, a liquid reagent, a liquid adhesive, a liquid food product, a liquid metal (e.g., a solder), and/or any other liquid In another embodiment, the cartridge can further comprise a sensor for metering fluid dispensed by the outlet conduit. For instance, this sensor may be a capacitive or optical sensor.

In another embodiment, the cartridge can further comprise a coupling assembly for attaching the rotary valve and the plunger to an actuator assembly. This embodiment may be beneficial because it may enable the rotary valve and the plunger to be conveniently connected to an actuator. The coupling assembly in some embodiments may enable the rotary valve and the plunger to be actuated independently by the actuator assembly.

In some embodiments, it may be possible to have a cartridge with its own actuator. In this case, the cartridge can further comprise an actuator. In some cases, the actuator may be connected to the coupling assembly or the actuator may be designed or operable for directly actuating the rotary valve and the plunger independently.

A pumping unit as used here can encompass the rotary valve and plunger for pumping the fluid. When installed into an automatic analyzer, there may be one actuator per pumping unit or there may be one actuator which can be moved and used to actuate all of the cartridges within the automatic analyzer. In this case, there may be a mechanism for moving the relative positions between the cartridge and the single actuator. There may also be an actuator for a group of cartridges.

For example, there may be different configurations for the cartridge. In some embodiments, the cartridge may have a single pumping unit. This single pumping unit may have conduits connected to different reservoirs. This may enable the cartridge to pump different types of fluids from the same cartridge. In another example, the cartridge may have multiple pumping units, with each of the pumping units connected to one or more reservoirs via its rotary valve.

In some embodiments, the cartridge can comprise a pumping unit and an attachable reservoir. This embodiment may be beneficial, because a universal pumping unit can be created and reservoirs attached to it when needed. This may facilitate having a larger variety of fluids available. Reservoirs of different volumes may also be selected. Different pumping units may also be selected. Such different pumping units may for instance have plungers with a different stroke and/or diameter. This may affect the volume of the pumping unit. In some applications, it may be desirable to pump a larger volume more accurately and in other applications a smaller but more accurate pumping volume may be desired. So, the use of a pumping unit and an attachable reservoir can allow a modular concept which can allow the combination of reservoirs comprising different types and/or volumes of fluids with an pumping unit which can be optimized to dispense a defined volume of this fluid. This modular concept can provide a large set of optimized cartridges based on a small set of pumping units and/or reservoirs which can be combined in different ways. The assembly of the pumping unit and the attachable reservoir can be performed on the factory site as a manufacturing step during the cartridge production or on the user site, e.g. by assembling the pumping unit with the attachable reservoir before inserting the cartridge into an automatic analyzer.

In another embodiment, the rotary valve can comprise a cylindrical portion. The pumping chamber can be a cavity within the rotary valve. The pumping chamber can be formed by the cavity and the plunger. The cartridge can comprise a cartridge body with a cylindrical space for receiving the cylindrical portion. The rotary valve can rotate within the cylindrical space.

In another embodiment, the reservoir conduit and the outlet conduit can be located on the cylindrical space. The pumping chamber conduit can be located on the cylindrical portion.

In another embodiment, the cartridge can comprise multiple pumping units.

In another embodiment, the cartridge can comprise multiple reservoirs.

In another embodiment, the multiple reservoirs can be filled with different fluids.

An automatic analyzer for analyzing a biological sample is presented. The automatic system can hold a cartridge. The automatic analyzer can comprise an actuator assembly for actuation of the plunger and of the valve. The automatic analyzer can further comprise a controller for controlling the operation of the actuator assembly.

An automatic analyzer as used herein can encompass a system for automatically analyzing a biological sample. The automatic analyzer can comprise an actuator assembly for linear actuation of the plunger and for rotational actuation of the rotary valve. The actuator assembly can further actuate the plunger and the rotary valve independently. The automatic analyzer can further comprise a controller for controlling the operation of the actuator assembly.

In some embodiments, the automatic analyzer may be adapted for holding multiple cartridges. In this case, there may be a mechanism for providing relative movement between the cartridges and a reaction tube/cuvette. There may be one actuator per pumping unit or there may be one actuator used for multiple cartridges. In this case, there may be a mechanism or a robotic system for providing relative movement between the cartridge and the actuator. There may also be embodiments where there are multiple actuators each used for a group of cartridges. The group of cartridges can be predetermined or the group of cartridges may be determined on the fly. Alternatively, multiple actuators may be used for a cartridge or a group of cartridges, e.g. for different purposes like pre-dispensing or post-dispensing actions.

In another embodiment, the automatic analyzer can comprise the cartridge.

In another embodiment, the controller can control the actuator assembly to rotate the pumping chamber conduit to connect with the reservoir conduit by rotating the rotary valve. The controller can further control the actuator assembly to fill the pumping chamber by increasing the volume of the pumping chamber with the plunger. The controller can further control the actuator assembly to rotate the pumping chamber conduit to connect with the outlet conduit by rotating the rotary valve. The controller can further control the actuator assembly to pump the fluid through the outlet conduit by decreasing the volume of the pumping chamber with the plunger. This embodiment may be beneficial because it can provide a method of pumping fluid through the outlet conduit.

In another embodiment, the controller can control the actuator assembly to receive the fluid from the outlet conduit by increasing the volume of the pumping chamber with the plunger.

In another embodiment, the controller can control the actuator assembly to rotate the pumping chamber conduit to connect with the reservoir conduit by rotating the rotary valve. The controller can further control the actuator assembly to return the fluid to the reservoir by decreasing the volume of the pumping chamber with the plunger. This embodiment may be advantageous because it provides operation of the pump without priming. One hundred percent or nearly 100% of the fluid may be used.

In another embodiment, the controller can control the actuator assembly to rotate the pumping chamber conduit to connect with the reservoir conduit by rotating the rotary valve. The controller can further control the actuator assembly to mix the fluid in the reservoir by repeatedly increasing and decreasing the volume of the pumping chamber with the plunger. In the case where the fluid contains beads or particles such as, for example, magnetic or latex beads, this embodiment may be used to mix the fluid and its compounds.

In another embodiment, the cartridge can comprise an outlet nozzle. The automatic analyzer can further comprise a meniscus detector for detecting a meniscus of the fluid. The controller can control the actuator to force fluid through the outlet nozzle. The controller can further detect the meniscus using the meniscus detector. The controller can further control the actuator to halt the forcing of fluid through the outlet when the meniscus can be in a predetermined location. This embodiment may be beneficial because it may enable more accurate and more precise dispensing of the fluid. This embodiment may be beneficial because if the meniscus is in the same place when the fluid dispensing starts then the dispensing of the fluid may be more accurate, more precise and/or more reproducible. The meniscus may be inside or outside the outlet nozzle. For instance, the outlet nozzle may be a long tube-like structure and the meniscus may have a particular position within the tube. In other embodiments, the meniscus may be formed by a drop of the fluid hanging from the outlet nozzle. In many applications, the meniscus can be positioned right at the orifice of the outlet nozzle.

In another embodiment, the controller can further control the actuator to force a predetermined volume of fluid through the outlet. In some embodiments, the actuator may be controlled to force the predetermined volume of fluid through the outlet nozzle after the meniscus is in the predetermined location.

In another embodiment, the meniscus detector can be any one of the following: a capacitive sensor, an optical sensor and a camera. When the meniscus is inside of the nozzle, a capacitive sensor may be used to detect the location of the meniscus. In case the nozzle is optically transparent, an optical sensor may also be used to determine the location of the meniscus within the nozzle. If the meniscus extends beyond the nozzle, then a capacitive sensor, an optical sensor or a camera may each be used to determine the location of the meniscus.

In another embodiment, the automatic analyzer is operable to hold multiple cartridges.

In another embodiment, the automatic analyzer can further comprise the multiple cartridges.

The embodiment with the multiple cartridges may be implemented in a variety of ways. For example, each pumping unit may have its own actuator assembly. This may be a parallel operation. In another example, cartridges may be moved and put onto the same actuator assembly or an actuator assembly may be moved between different cartridges or even between different pumping units that can be part of the same cartridge. In other embodiments, there may be multiple actuators and cartridges can be moved via a mechanical robotic system between these multiple actuators.

In another embodiment, the automatic analyzer can comprise a sensor or metering system operable for measuring or metering the dispensing of the fluid. The controller can control the dispensing of the fluid in accordance with measurements or data received from the sensor or metering system. In other words, the controller can form a closed loop control system with the sensor or metering system for controlling the dispensing of the fluid.

A method of operating a cartridge is presented. The method can comprise rotating the rotary valve to rotate the pumping chamber conduit to connect with the reservoir conduit, increasing the volume of the pumping chamber with the plunger to fill the pumping chamber, rotating the rotary valve to rotate the pumping chamber conduit to connect with the outlet conduit, and decreasing the volume of the pumping chamber with the plunger to pump the fluid through the outlet conduit.

In another embodiment, the method can further comprise increasing the volume of the pumping chamber with the plunger to retrieve the fluid from the outlet conduit.

In another embodiment, the method can further comprise rotating the rotary valve to rotate the pumping chamber conduit to connect with the reservoir conduit and decreasing the volume of the pumping chamber with the plunger to return the fluid to the reservoir.

In another embodiment, the method can further comprise rotating the rotary valve to rotate the pumping chamber conduit to connect with the reservoir conduit and repeatedly increasing and decreasing the volume of the pumping chamber with the plunger to mix the fluid in the reservoir.

A cartridge for dispensing fluid is presented. The cartridge can comprise a slide valve. The slide valve can have rectilinear motion. The slide valve may also be referred to as a rectilinear valve. The slide valve can comprise a pumping chamber for pumping the fluid. The slide valve can translate a pumping chamber conduit. The pumping chamber conduit can be connected with the pumping chamber. The cartridge can further comprise a plunger for changing the volume of the pumping chamber. The cartridge can further comprise a reservoir for storing the fluid. The cartridge can further comprise a reservoir conduit for connecting the reservoir with the slide valve. The slide valve can translate the pumping chamber conduit to connect with the reservoir conduit. The cartridge can further comprise an outlet conduit for dispensing the fluid. The slide valve can further translate the pumping chamber conduit to connect with the outlet conduit. This embodiment may be beneficial because the combination of the slide valve and the plunger can allow accurate dispensing of the fluid. Further, the embodiment may also enable a reduced amount of waste fluid produced when dispensing fluid by the cartridge.

Embodiments may also have the advantage that a large set of pumping actions by the pumping chamber can be possible. This embodiment may have the advantage that a large variety of pumping actions can be performed with the pumping chamber by controlling the translation position of the slide valve and properly operating the plunger. For instance, the slide valve may be positioned such that the pumping chamber conduit can be connected to the reservoir conduit. In this case, the plunger may be used to either withdraw fluid from the reservoir into the pumping chamber or may be used to pump the fluid from the pumping chamber back into the reservoir.

The present embodiment may enable other types of actions using the pumping chamber. For instance, when the pumping chamber conduit is aligned or connected with the reservoir conduit, the plunger may be repeatedly used to increase and decrease the volume of the pumping chamber. This may enable the fluid within the reservoir to be mixed. Also the ability to put the fluid back into the reservoir may reduce the amount of fluid that may be wasted.

This embodiment may also enable a so-called reduced waste priming or non-waste priming function of the pumping chamber whereby none or possibly only a very small amount of the fluid is wasted or discarded when fluid is pumped out through the outlet conduit. For instance, when the pumping chamber conduit is connected with the outlet conduit, the plunger may be used to decrease the volume of the pumping chamber and thereby force or dispense fluid out through the outlet conduit. During the process of doing this, there may be fluid within the outlet conduit which may not exit the outlet conduit. After the correct amount of fluid has been dispensed, the plunger may then be used to increase the volume of the pumping chamber thereby withdrawing fluid that may remain within the outlet conduit back into the pumping chamber. Fluid can then be held within the pumping chamber or if the slide valve is translated into alignment with the reservoir conduit, the fluid which was previously within the outlet conduit may be pumped back into the reservoir.

The slide valve may also provide a method of preventing fluid from accidentally leaking from the reservoir. For instance, the slide valve may be able to be translated in some embodiments to a position where it can neither be aligned with the outlet conduit nor with the reservoir conduit. This may prevent fluid and/or gas from exiting from the outlet conduit and/or from fluid and/or gas in a reservoir leaking or draining into the pumping chamber.

In some embodiments, the cartridge can comprise a pumping unit and an attachable reservoir. This embodiment may be beneficial, because a universal pumping unit can be created and reservoirs attached to it when needed. This may facilitate having a larger variety of fluids available. Reservoirs of different volumes may also be selected. Different pumping units may also be selected. Such different pumping units may for instance have plungers with a different stroke and/or diameter. This may affect the volume of the pumping unit. In some applications, it may be desirable to pump a larger volume more accurately and in other applications a smaller but more accurate pumping volume may be desired.

The use of a pumping unit and an attachable reservoir may allow to realization of a modular system which can allow the combination of reservoirs comprising different types and/or volumes of fluids with an pumping unit which can be optimized to dispense a defined volume of this fluid. This modular system may provide a large set of optimized cartridges based on a small set of pumping units and/or reservoirs which can be combined in different ways. The assembly of the pumping unit and the attachable reservoir can be performed on the factory site as a manufacturing step during the cartridge production or on the user site, for example, by assembling the pumping unit with the attachable reservoir before inserting the cartridge into an automatic analyzer.

The reservoir can be constructed in a variety of ways. In some embodiments, the reservoir may be a hard walled chamber, preferably made of plastics using injection moulding or thermoforming processes. In some embodiments, the reservoir may be a chamber with a flexible wall. In some embodiments, the reservoir can be a pouch or bladder. In other embodiments, the reservoir can be a pouch or bladder supported by an outer container. In other embodiments, the reservoir can be a tube.

In some embodiments, the pumping chamber conduit can be aligned with the reservoir conduit and/or outlet conduit using mechanical stops. As an alternative to using mechanical stops, the alignment can also be achieved by other means, for example, by spatially defined changes of physical or geometrical properties, for example, by changes in friction coefficients or diameter. In other embodiments, mechanical stops may not be used and the alignment can be performed by an actuator system which can be attached to the cartridge during use.

In another embodiment, the cartridge can further comprise an outlet nozzle connected to the outlet conduit. An outlet nozzle as used herein can encompass a nozzle design to minimize the waste of fluid and may enable drops to cleanly drip during the dosing process. For instance, in a simple tube, a drop of the fluid may hang outside the nozzle after the plunger is used to decrease the volume of the pumping chamber. The shape or function of the outlet nozzle can be designed to reduce the chances of a drop of the fluid hanging on it. For instance, the outlet nozzle may have a so-called duckbill shape and be a duckbill nozzle.

In other embodiments, the cartridge may have additional reservoirs and additional reservoir conduits which can enable the pumping chamber to be connected to these additional reservoirs. Typically, a cartridge may contain only a single fluid or reagent. In some embodiments, this may be a diluent that can be used or required for various tests. There may also be multiple reservoirs which may be each connected to a conduit accessible to the pumping chamber conduit at a particular rectilinear position of the slide valve.

For example, for many clinical tests, there may be two reservoirs and, for immunoassays, there may be two or three different fluids within different reservoirs. In some embodiments, the cartridge may have multiple pumping units, with each of the pumping units being connected to one or more reservoirs via its slide valve. In this way, the immunoassays can be dispensed using separate pumping units and they may not be mixed by the pumping process.

In some embodiments, the slide valve and the plunger can be actuated independently. In other embodiments, the plunger or the actuation of the plunger can be used to also actuate the slide valve.

In another embodiment, the cartridge can further comprise a return conduit connected to the reservoir. The pumping chamber conduit can receive fluid from a first portion of the reservoir. The return conduit can return fluid to a second portion of the reservoir. The slide valve can further translate the pumping chamber conduit to connect to the return conduit. This embodiment may have the benefit of reducing the number of bubbles within the first portion of the reservoir by transmitting the bubbles to the second portion of the reservoir.

For instance, fluid can be drawn from the reservoir when the slide valve is translated such that the pumping chamber conduit can be in alignment with the reservoir conduit. After a certain amount of the fluid has been dispensed through the outlet conduit, the slide valve may be translated into such a position such that the pumping chamber conduit can be in alignment with the return conduit. The reservoir conduit may draw fluid from one portion of the reservoir and the return conduit can be used to return the fluid to a different portion of the reservoir. For instance, the two locations of the reservoir conduit and the return conduit can be far enough away that it can be unlikely that bubbles which enter the reservoir through the return conduit are drawn into the reservoir conduit when fluid is drawn from the reservoir into the pumping chamber.

In another embodiment, the cartridge can further comprise a secondary reservoir. The cartridge can further comprise a secondary reservoir conduit. The slide valve can further translate the pumping chamber conduit to connect to the secondary reservoir conduit. This embodiment may be beneficial because it may enable a second or distinct fluid to be stored and dispensed using the cartridge, it may also enable waste fluid to be disposed of in the secondary reservoir.

In another embodiment, the secondary reservoir can comprise a vent. A vent as used herein can be a structure which can enable air bubbles or other gas volumes to enter or leave the cartridge. Alternatively, the reservoir can comprise such a vent or both the reservoir and the secondary reservoir can comprise such vents.

It should be noted that additional reservoirs may be added to the cartridge by adding a third reservoir and a third reservoir conduit, a fourth reservoir and a fourth reservoir conduit, and so on so that any number of reservoirs and reservoir conduits may be added to the cartridge. The additional reservoirs may also comprise vents.

In another embodiment, the cartridge can further comprise a connecting conduit. The connecting conduit can transport fluid between the secondary reservoir and the reservoir. This embodiment may be beneficial because the connecting conduit may enable the secondary reservoir to be used as a place to deposit fluid in order to return it to the reservoir.

In another embodiment, the cartridge can comprise a membrane or grid or filter located within the connecting conduit. If a membrane is used, the membrane can be permeable to the fluid. Such membranes are described, for example, in "Unimpeded Permeation of Water Through Helium-Leak-Tight Graphene-Based Membranes" (R. R. Nair et al.; Science 335, 442 (2012). If a grid or mechanical filter is used, the mesh or hole size has to be smaller than the gas bubble size to prevent the gas bubbles from transition through the grid or filter. This embodiment may be beneficial because it may provide a means of filtering fluid or blocking of gas bubbles when fluid is returning from the secondary reservoir into the reservoir.

In another embodiment, the secondary reservoir can comprise a bubble guiding structure. A bubble guiding structure as used herein can encompass a structure which can be used to guide a gas bubble to a predetermined location in a reservoir or towards a vent.

In some implementations, the bubble guiding structure may allow fluid to pass around the bubble as it is moving through the reservoir. For instance, a bubble structure may be a set of ridges which can be used to position and guide a bubble. The structures and ridges may be spaced close enough together such that the surface tension of the fluid can prevent the bubble from going into regions which can allow the fluid to go around the bubble. This may be beneficial because if the bubble is not properly confined, the bubble may get stuck at a particular position in the secondary reservoir and not allowed to go to the top of the secondary reservoir or in the case where there can be a connecting conduit to allow the fluid to return to the reservoir.

In another embodiment, the reservoir and/or the secondary reservoir can comprise a vent. The vent can be sealed with a filter. The filter can be permeable to air. The filter can seal the fluid in the cartridge. The filter may be hydrophobic in some embodiments. In some embodiments, the gas filter may have micropores to only let gas through, but no liquids. In some embodiments, the filter may be, but is not limited to: a porous form of polytetrafluoroethylene, carbon fibers, carbon fibers coated with PTFE, carbon nanotubes, polymer fibers, or fluoropolymer fibers In another embodiment, the fluid can comprise magnetic beads, latex beads, a blood grouping reagent, an immune reagent, an antibody, an enzyme, a recombinant protein, a virus isolate, a virus, a biological reagent, a solvent, a diluent, a dispersion, nanoparticles, a protein, a salt, a detergent, a nucleic acid, an acid, a base or combinations thereof.

In other embodiments, the fluid can be a particle suspension, a liquid reagent, a liquid adhesive, a liquid food product, a liquid metal (for example, solder) or any other liquid.

In another embodiment, the cartridge can further comprise a sensor for metering fluid dispensed by the outlet nozzle. For instance, this sensor may be a capacitive or optical sensor.

In another embodiment, the cartridge can further comprise a coupling assembly for attaching the slide valve and the plunger to an actuator assembly. In some embodiments, the coupling assembly can only attach to the plunger. In other embodiments, the coupling assembly can attach to both the slide valve and to the plunger so that they may be actuated independently.

In some embodiments, it may be possible to have a cartridge with its own actuator. In this case, the cartridge can further comprise an actuator. In some cases, the actuator may be connected to the coupling assembly or the actuator may be designed or operable for directly actuating the slide valve and the plunger independently.

A pumping unit as used here can encompass the slide valve and plunger for pumping the fluid. When installed into an automatic analyzer, there may be one actuator per pumping unit or there may be one actuator which can be moved and used to actuate all of the cartridges within the automatic analyzer. In this case, there may be a mechanism for moving the relative positions between the cartridge and the single actuator. There may also be an actuator for a group of cartridges.

For example, there may be different configurations for the cartridge. In some embodiments, the cartridge may have a single pumping unit. This single pumping unit may have conduits connected to different reservoirs. This may enable the cartridge to pump different types of fluids from the same cartridge. In another example, the cartridge may have multiple pumping units, with each of the pumping units connected to one or more reservoirs via its slide valve.

In another embodiment, the cartridge can comprise multiple pumping units or multiple reservoirs. In another embodiment, the multiple reservoirs can be filled with different fluids.

In another embodiment, the slide valve can comprise a piston. The pumping chamber can be a cavity within the piston. The pumping chamber can be formed by the cavity and the plunger. The piston can be operable for translational motion within the volume.

The piston and the volume may have different cross-sectional shapes which can correspond to each other. For instance, both the piston and the corresponding volume may have a round, oval, or other cross-sectional shape.

In another embodiment, the piston and the slide valve can be operable for co-linear motion. In other words, the piston and the slide valve can be operable to have translational motion that can be parallel or in the same direction.

In another embodiment, the slide valve can comprises\a reservoir conduit mechanical stop for aligning the pumping chamber conduit with the reserve conduit. In other words, there can be a mechanical stop which can align the piston such that the pumping chamber conduit can be aligned with the reservoir conduit.

In another embodiment, the slide valve can comprise an outlet conduit mechanical stop for aligning the pumping chamber conduit with the outlet conduit. In other words, the slide valve can have a mechanical stop which can align the piston such that the pumping chamber conduit can line up with the outlet conduit.

In another embodiment, the piston can comprise two plunger mechanical stops for limiting the motion of the plunger relative to the piston. The plunger can actuate the piston. This embodiment may be beneficial because it can enable the cartridge to be operated with a single linear actuator. This can be particularly true when there can be the combined embodiments of also having a reservoir conduit mechanical stop and an outlet conduit mechanical stop.

An automatic analyzer for analyzing the biological sample is presented. The automatic analyzer can hold a cartridge. The automatic analyzer can comprise an actuator assembly operable for linear actuation of the plunger and the slide valve. The actuator assembly may have either one or two actuators depending upon the design of the cartridge. For instance, in some embodiments, the linear actuator may only actuate the plunger. In other embodiments, there may be a linear actuator which can actuate the slide valve and the plunger independently. The automatic analyzer can further comprise a controller for controlling the operation of the actuator assembly.

In another embodiment, the automatic analyzer can comprise the cartridge.

In another embodiment, the automatic analyzer can hold a cartridge. The piston can comprise two plunger mechanical stops for limiting the motion of the plunger relative to the piston and where the plunger can actuate the piston. The actuator assembly is operable for linear actuation of the plunger. This embodiment may be beneficial because only a single linear actuator is used. The actuation of the slide valve can be done through or by the plunger.

In another embodiment, the actuator assembly can be operable for a separate linear actuation of the plunger and for the linear actuation of the slide valve. In this embodiment, there can be two linear actuators in the actuator assembly and the plunger and the slide valve can be actuated independently. This embodiment may be beneficial because it can enable more complex behavior or pumping protocols by the automatic analyzer.

In another embodiment, the controller can control the actuator assembly to translate the pumping chamber conduit to connect with the reservoir conduit by translating the slide valve. The controller can further control the actuator assembly to fill the pumping chamber by increasing the volume of the pumping chamber with a plunger. The controller can further control the actuator assembly to translate the pumping chamber conduit to connect with the outlet conduit by translating the slide valve. The controller can further control the actuator assembly to pump the fluid through the outlet conduit by decreasing the volume of the pumping chamber with the plunger.

Translating the slide valve can be equivalent herein to translating the piston in those embodiments where the slide valve can have a piston.

In another embodiment, the controller can control the actuator assembly to translate the pumping chamber conduit to connect with the reservoir conduit by translating the slide valve. The controller can further control the actuator assembly to return the fluid to the reservoir by decreasing the volume of the pumping chamber with a plunger. This embodiment may be advantageous because it can provide operation of the pump without priming. One hundred percent or nearly 100% of the fluid may be used.

In another embodiment, the controller can control the actuator assembly to translate the pumping chamber conduit to connect with the reservoir conduit by translating the slide valve. The controller can further control the actuator assembly to mix the fluid in the reservoir by repeatedly increasing and decreasing the volume of the pumping chamber with the plunger. In the case, where the fluid comprises beads or particles such as, for example, magnetic or latex beads, this embodiment may be used to mix the fluid and its compounds.

In another embodiment, the controller can further control the actuator assembly to retrieve fluid from the outlet conduit by increasing the volume of the pumping chamber with the plunger.

In another embodiment, the cartridge can comprise an outlet nozzle. The automatic analyzer can further comprise a meniscus detector for detecting the meniscus of the fluid. The controller can further control the actuator assembly to force fluid through the outlet nozzle. The controller can further detect the meniscus using the meniscus detector. The controller can further control the actuator to halt the forcing the fluid through the outlet when the meniscus is in a predetermined location. This embodiment may be beneficial because it may enable more accurate and more precise dispensing of the fluid. This embodiment may be beneficial because if the meniscus is in the same place when the fluid dispensing starts, then the dispensing of the fluid may be more accurate, more precise and/or more reproducible. The meniscus may be inside or outside the outlet nozzle. For instance, the outlet nozzle may be a long tube-like structure and the meniscus may have a particular position within the tube. In other embodiments, the meniscus may be formed by a drop of the fluid hanging from the outlet nozzle. In many applications, the meniscus can be positioned right at the orifice of the outlet nozzle.

In another embodiment, the controller can further control the actuator to force a predetermined volume of fluid through the outlet. In some embodiments, the actuator may be controlled to force the predetermined volume of fluid through the outlet nozzle after the meniscus is in the predetermined location.

In another embodiment, the meniscus detector can be any one of the following: a capacitive sensor, an optical sensor and a camera. When the meniscus is inside of the nozzle, a capacitive sensor may be used to detect the location of the meniscus. In case the nozzle is optically transparent, an optical sensor may also be used to determine the location of the meniscus within the nozzle. If the meniscus extends beyond the nozzle, then a capacitive sensor, an optical sensor or a camera may each be used to determine the location of the meniscus.

In another embodiment, the automatic analyzer can hold multiple cartridges. In another embodiment, the automatic analyzer can further comprise the multiple cartridges.

The embodiment with the multiple cartridges may be implemented in a variety of ways. For example, each pumping unit may have its own actuator assembly. This may be a parallel operation. In another example, cartridges may be moved and put onto the same actuator assembly or an actuator assembly may be moved between different cartridges or even between different pumping units that can be part of the same cartridge. In yet another embodiment, there may be multiple actuators and cartridges that can be moved via a mechanical robotic system between these multiple actuators.

In another embodiment, the automatic analyzer can hold multiple cartridges. In this case, there may be a mechanism for providing relative movement between the cartridges and a reaction tube/cuvette. There may be one actuator per pumping unit or there may be one actuator used for multiple cartridges. In this case, there may be a mechanism or a robotic system for providing relative movement between the cartridge and the actuator. There may also be embodiments where there can be multiple actuators each used for a group of cartridges. The group of cartridges can be predetermined or the group of cartridges may be determined on the fly. Alternatively, multiple actuators may be used for a cartridge or a group of cartridges, for example, for different purposes like pre-dispensing or post-dispensing actions.

In another embodiment, the automatic analyzer can comprise a sensor or metering system for measuring or metering the dispensing of the fluid. The controller can control the dispensing of the fluid in accordance with measurements or data received from the sensor or metering system. In other words, the controller can form a closed loop control system with the sensor or metering system for controlling the dispensing of the fluid.

A method of operating the cartridge is presented. The method can comprise translating the slide valve to translate the pumping chamber conduit to connect with the reservoir conduit. The method can further comprise increasing the volume of the pumping chamber with the plunger to fill the pumping chamber. The method can further comprise translating the slide valve to translate the pumping chamber conduit to connect with the outer outlet conduit. The method can further comprise decreasing the volume of the pumping chamber with the plunger to pump the fluid through the outlet conduit.

Embodiments descriptive of an automatic analyzer may also be applicable to an automatic system for dispensing fluids.

An automatic system for dispensing fluids is presented. The automatic system can hold a cartridge. The automatic system can comprise an actuator assembly for linear actuation of the plunger and of the slide valve. The automatic system can further comprise a controller for controlling the operation of the actuator assembly. In another embodiment, the actuator assembly can be operable for linear actuation of the plunger. In another embodiment, the automatic system can be operable for separate linear actuation of the plunger and for linear actuation of the slide valve.

In another embodiment, the cartridge can comprise an outlet nozzle. The automatic analyzer can further comprise a meniscus detector for detecting a meniscus of the fluid. The controller can control the actuator assembly to force fluid through the outlet nozzle; detect the meniscus using the meniscus detector; and control the actuator to halt the forcing of fluid through the outlet when the meniscus is in a predetermined location.

Referring initially to FIG. 1, FIG. 1 illustrates a cartridge 100 and an actuator assembly 102. The actuator assembly 102 can comprise a linear actuator 104 which can be able to actuate in direction 105. The actuator assembly 102 can further comprise a rotational actuator 106 able to actuate in the direction 107.

The cartridge 100 can comprise a plunger 108 and a rotary valve 110. The cartridge 100 can comprise a cartridge body 112 which can have a cylindrical space 116. In this case, the cylindrical space 116 can be formed by a bearing material. The rotary valve 110 can have at least a cylindrical portion 114 adapted to fit into the cylindrical space 116 of the cartridge body 112. The rotary valve 110 can have a hollow space which can form a pumping chamber 118 which can be formed by the hollow space and the plunger 108. The pumping chamber 118 can have a pumping chamber conduit 120 which can be formed in a wall of the rotary valve 110. The rotary valve 110 can rotate within the cylindrical space 116 to position the pumping chamber conduit 120 at different angular positions.

The cartridge 100 can further comprise a reservoir 122 for being filled with a liquid. The cartridge 100 may also comprise a vent for allowing gas to be vented into the reservoir 122. The cartridge 100 can further comprise a reservoir conduit 124. The reservoir conduit 124 can provide the reservoir 122 access to the pumping chamber conduit 120 when the pumping chamber conduit is in the correct rotational position. The cartridge 100 can also comprise an optional outlet nozzle 126 for dispensing the fluid. The outlet nozzle 126 can be connected to an outlet conduit 128. The outlet conduit 128 can allow the pumping chamber 118 to dispense the fluid. The outlet conduit 128 in this embodiment can be connected to the outlet nozzle 126 when the pumping chamber conduit 120 is in the correct rotational position. There can be a coupling assembly 130 which can couple the actuator assembly 102 to the cartridge 100. The coupling assembly 130 can be designed for being and actuating the piston 108 in the linear direction 105. The coupling assembly 130 can also be adapted to independently rotate the rotary valve 110. For instance, there may be grooves cut into the rotary valve 110 and there may be a shape on the coupling assembly 130 which can mate into the groove of the rotary valve 110. The example shown in FIG. 1 is only one way in which the rotary valve 110 and the piston 108 may be actuated. Other equivalent mechanisms may also be used to actuate and attach to the rotary valve 110 and the piston 108.

FIG. 2 illustrates four views 200, 202, 204, 206 of the cartridge 100. FIG. 2 illustrates how the cartridge 100 may be used to pump fluid through the outlet conduit 128. In view 200, the pumping chamber conduit 120 can be aligned with the reservoir conduit 124. The plunger 108 can be fully depressed and the pumping chamber 118 can have no volume or can be extremely small. In this example, the plunger 108 can be fully depressed. However, fully depressing the plunger 108 may not be a requirement for the operation. In the examples described herein, the relative motion of the plunger is what is relevant. For example, depressing the plunger 108 can cause the volume of the pumping chamber to decrease and this can force the fluid through the outlet conduit.

Next in view 202, the plunger can be withdrawn in direction 208. This can cause fluid from the reservoir 122 to enter the pumping chamber 118. Next in view 204, the rotary valve 110 can be rotated 210 such that the pumping chamber conduit 120 can be aligned with the outlet conduit 128. The pumping chamber 118 can now be isolated from the reservoir 122. Next in view 206, the plunger 108 can be depressed in direction 212 and fluid 214 can exit via the outlet conduit 128.

FIG. 3 illustrates a pumping method similar to that shown in FIG. 2 except additional steps are performed to remove fluid from the outlet nozzle 126 and the outlet conduit 128. The same views 202, 204 and 206 are again shown. There are three additional views 300, 302 and 304 of the cartridge 100 presented. The step according to view 300 can be performed after view 206. The plunger 108 can be withdrawn in the direction 306 to withdraw fluid from the outlet nozzle 126 in the outlet conduit 128. In this example, the plunger 108 can be withdrawn enough such that a bubble 208 can form in the pumping chamber 118. Next in view 302, the rotary valve 110 can be rotated in direction 310 such that the pumping chamber conduit 120 can be aligned with the reservoir conduit 124. Finally in view 304, the plunger 108 can be depressed in direction 312 thereby forcing fluid out of the pumping chamber 118 into the reservoir 122. In addition, the bubble 308 can also be forced into the reservoir 122.

FIGS. 4A and 4B shows seven views 400, 402, 404, 406, 408, 410, 412 of a different embodiment of a cartridge 414. In this embodiment, the cartridge 414 can have a reservoir 122 and a secondary reservoir 416. FIG. 4 illustrates how fluid 214 can be pumped through the outlet conduit 128 where the fluid can be taken from the reservoir 122 and then excess fluid from the outlet nozzle 126 and outlet conduit 128 can be pumped into the secondary reservoir 416. In this cartridge 414, it can be seen that there can be a connecting conduit 418 between the reservoir 122 and the secondary reservoir 416. The connecting conduit 418 may not be necessarily present in all embodiments. In some alternative embodiments, there can also be a membrane which can be permeable to the fluid may be placed some place in the connecting conduit 418. View 400 shows the plunger 108 as being fully depressed and the pumping chamber conduit 120 being aligned with the reservoir conduit 124. Next in view 402, the plunger can be withdrawn in direction 420 filling the pumping chamber 118 with the fluid 214. Next in view 404, the rotary valve 110 can be rotated such that the pumping chamber conduit 120 can be aligned with the outlet conduit 128.

The rotary valve can be rotated in direction 422. Next in view 406, the plunger 108 can be depressed in direction 424 and fluid 214 can be forced out of the outlet conduit 128. Next in view 408, the plunger 108 can be withdrawn in the direction 426 to withdraw the fluid 214 that was previously in the outlet conduit 128 and the pumping chamber conduit 120 back into the pumping chamber 118. Next in view 410, a rotary valve 110 can be rotated in direction 428 to align the pumping chamber conduit 120 with the secondary reservoir conduit 430. Finally in view 412, the plunger 108 can be depressed in direction 432 driving the bubble 308 and the fluid 126 into the secondary chamber 416. In some embodiments, the secondary chamber 416 may have a vent to atmosphere. In some embodiments, the vent may be covered with a filter which can allow gas to pass but which can keep the fluid 416 from exiting the cartridge 414. In view 412, the pumping chamber conduit 120 and the secondary reservoir conduit 430 are shown filled with the bubble 308.

Figure 5:
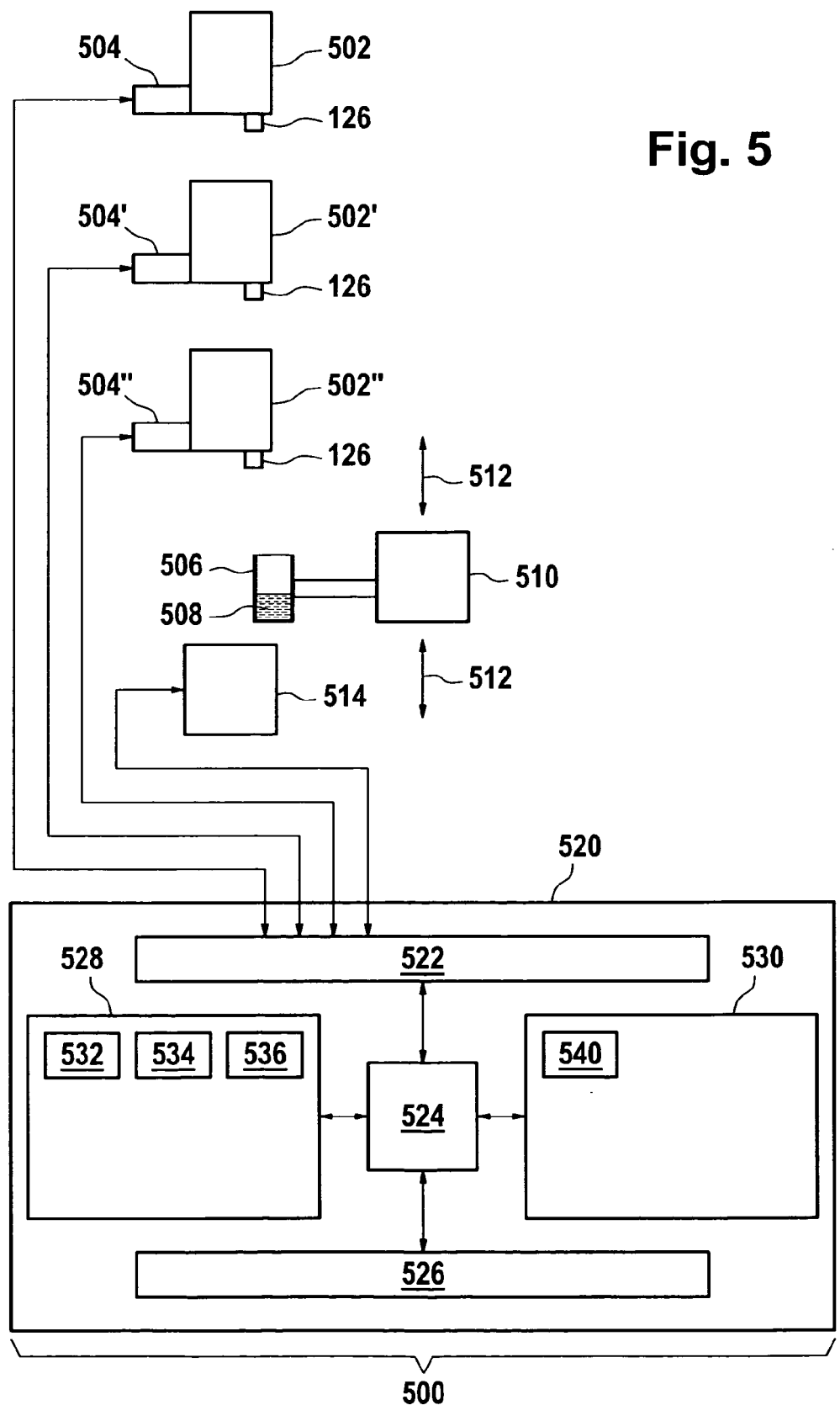
FIG. 5 illustrates an automatic analyzer according to an embodiment of the present disclosure.

FIG. 5 illustrates an automatic analyzer 500. This automatic analyzer is shown as having three cartridges 502, 502' and 502". There can be an actuator assembly 504 connected to cartridge 502. There can be an actuator assembly 504' attached to cartridge 502'. There can be an actuator assembly 504" attached to cartridge 502". The actuator assemblies 504, 504', 504" can actuate the rotary valve and plunger of the cartridges 502, 502', 502". The automatic analyzer 500 is shown as having a relative mover 510 which provides relative movement 512 between a reagent container or cuvette 506 and the cartridges 502, 502' and 502". The reagent container or cuvette 506 is shown as containing a biological sample 508. The cartridges 502, 502', 502" may be used to add one or more fluids to the biological sample 508. The automatic analyzer 500 is shown as further comprising a sensor system 514. The sensor system can comprise one or more sensors for measuring a quantity or a physical or chemical or biochemical property of the biological sample 508. For example, the sensor system 514 may comprise an nuclear magnetic resonance (NMR) system, an optical transmission or reflectance measurement system, a pH meter, a camera system, a polymerase chain reaction (PCR) apparatus, a Electrochemiluminescence (ECL) apparatus, a spectroscopic measurement system, an electrochemical or an optical sensor, and a chromatography system. The relative mover 510 can also move the reagent container or cuvette 506 to the sensor system 514.

The arrangement of the cartridges 502, 502', 502" and the sensor system 514 is representative. In some embodiments, the reagent container or cuvette 506 may remain in a fixed position and the cartridges 502, 502', 502" may move. The actuation systems 504, 504', 504" and the sensor system 514 are shown as being connected to a hardware interface 522 of a computer system 520. The computer system 520 can function as a controller for the automatic analyzer 500. The computer 520 is further shown as comprising a processor 524 which can control the operation and function of the automatic analyzer 500 using the hardware interface 522. The processor 524 is shown as further being connected to a user interface 526, computer storage 528 and computer memory 530. The computer storage 528 is shown as comprising an analysis request 532. The analysis request 532 can comprise a request to analyze the biological sample 508.

The computer storage 528 is shown as further comprising sensor data 534 received from the sensor system 514. The computer storage 528 is shown as further comprising an analysis result 536 which can be determined using the sensor data 534. The computer memory 530 can comprise a control module 540. The control module 540 can comprise computer executable code which can enable the processor 524 to control the operation and function of the automatic analyzer 500. For instance, the control module 540 may use the analysis request 532 to generate commands to generate and send to the actuation systems 504, 504', 504", the sensor system 514 and the relative movement system 510. The control module 540 may also generate the analysis result 536 using the sensor data 534.

Various algorithms may be used for controlling the dispensing of the fluid in different embodiments. For instance, the actuator assembly may be controlled by the processor to perform a series of predetermined actions to dispense the fluid. In another example, a sensor or metering system can be integrated into the automatic analyzer to measure the dispensing of the fluid. In this case, an algorithm can use the actuator assembly and the sensor to form a closed loop feedback to accurately control or meter the dispensing of the fluid.

Figure 6:
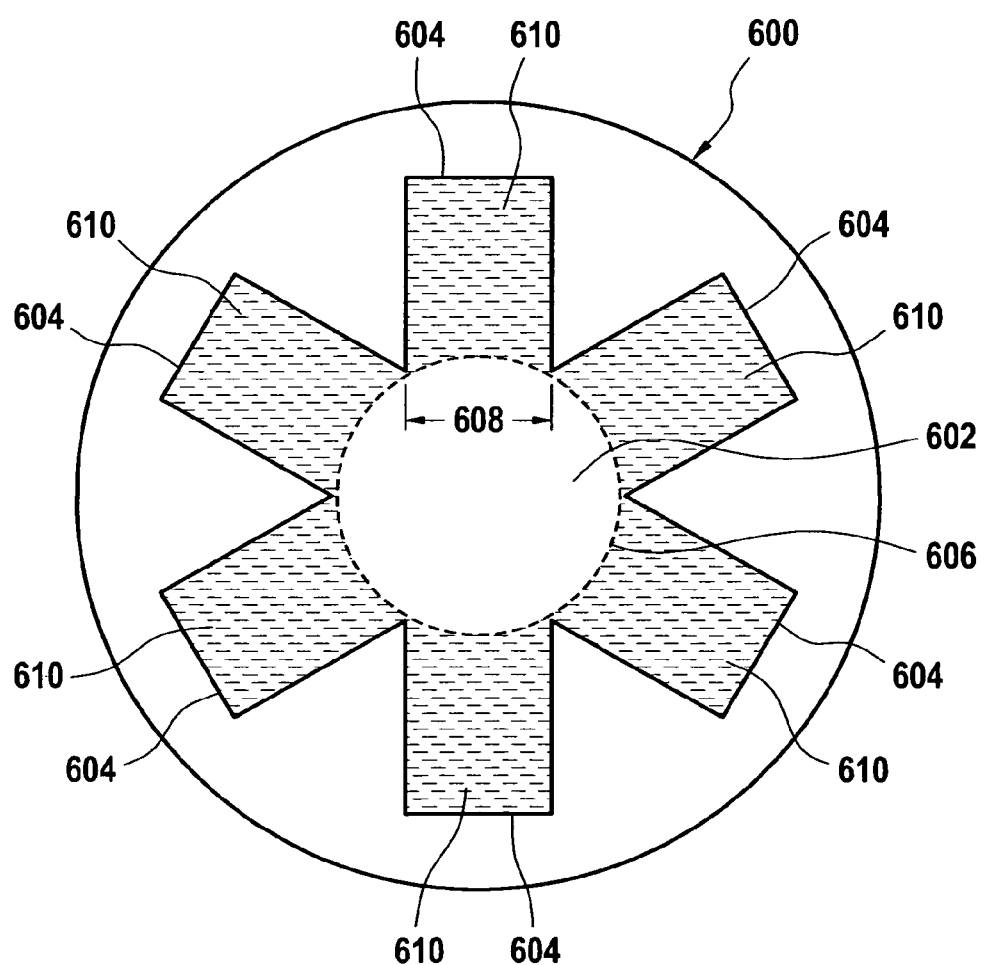
FIG. 6 illustrates a bubble guide according to an embodiment of the present disclosure.

FIG. 6 illustrates a bubble guiding structure 600. The bubble guiding structure 600 may for instance be located within a reservoir or secondary reservoir of a cartridge. The bubble guiding structure 600 can comprise a bubble channel 602 surrounded by various fluid channels 604. The bubble channel 602 can provide a path for a bubble 606. The fluid channels 604 can have a space or width 608 which can be narrow enough such that the bubble 606 can be prevented from entering the fluid channel 604 by the surface tension of the fluid. The bubble channel 602 can confine the bubble 606 and can allow the bubble to rise while allowing the fluid 610 to go around the bubble.

Figure 7:
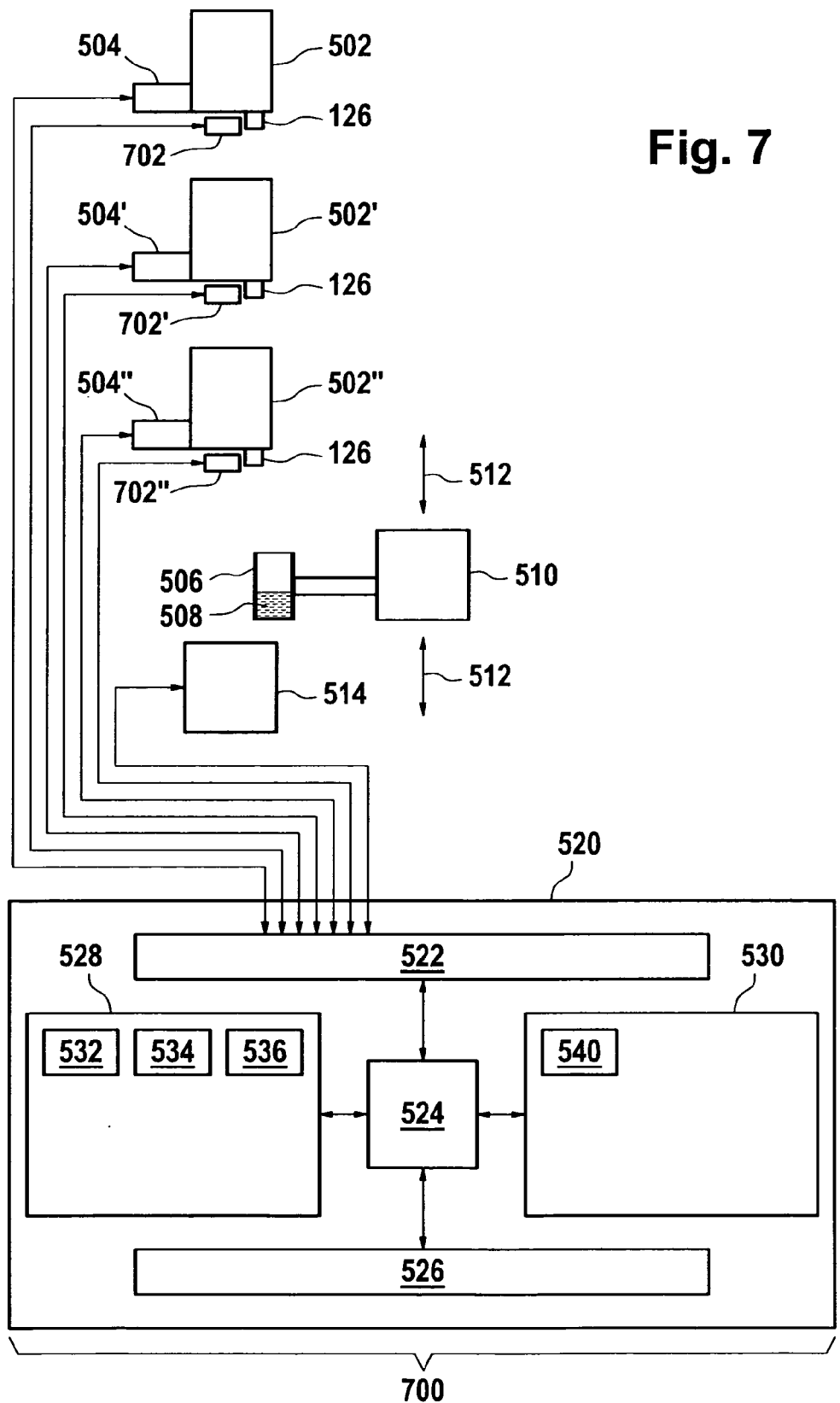
FIG. 7 illustrates an automatic analyzer according to another embodiment of the present disclosure.

FIG. 7 illustrates an automatic analyzer 700. The automatic analyzer 700 is similar to the automatic analyzer 500 shown in FIG. 5. The automatic analyzer 700 of FIG. 7 additionally has a meniscus detector 702, 702', 702". Each meniscus detector 702, 702', 702" can be positioned adjacent to the outlet nozzle 126. The meniscus detector 702, 702', 702" can each be connected to the hardware interface 522. This can enable the processor 524 to control the actuator assemblies 504, 504', 504" to control the location of the meniscus. This for instance may enable the processor to more accurately and or reproducibly dispense fluid from the cartridges 502, 502', 502".

Figure 8A:
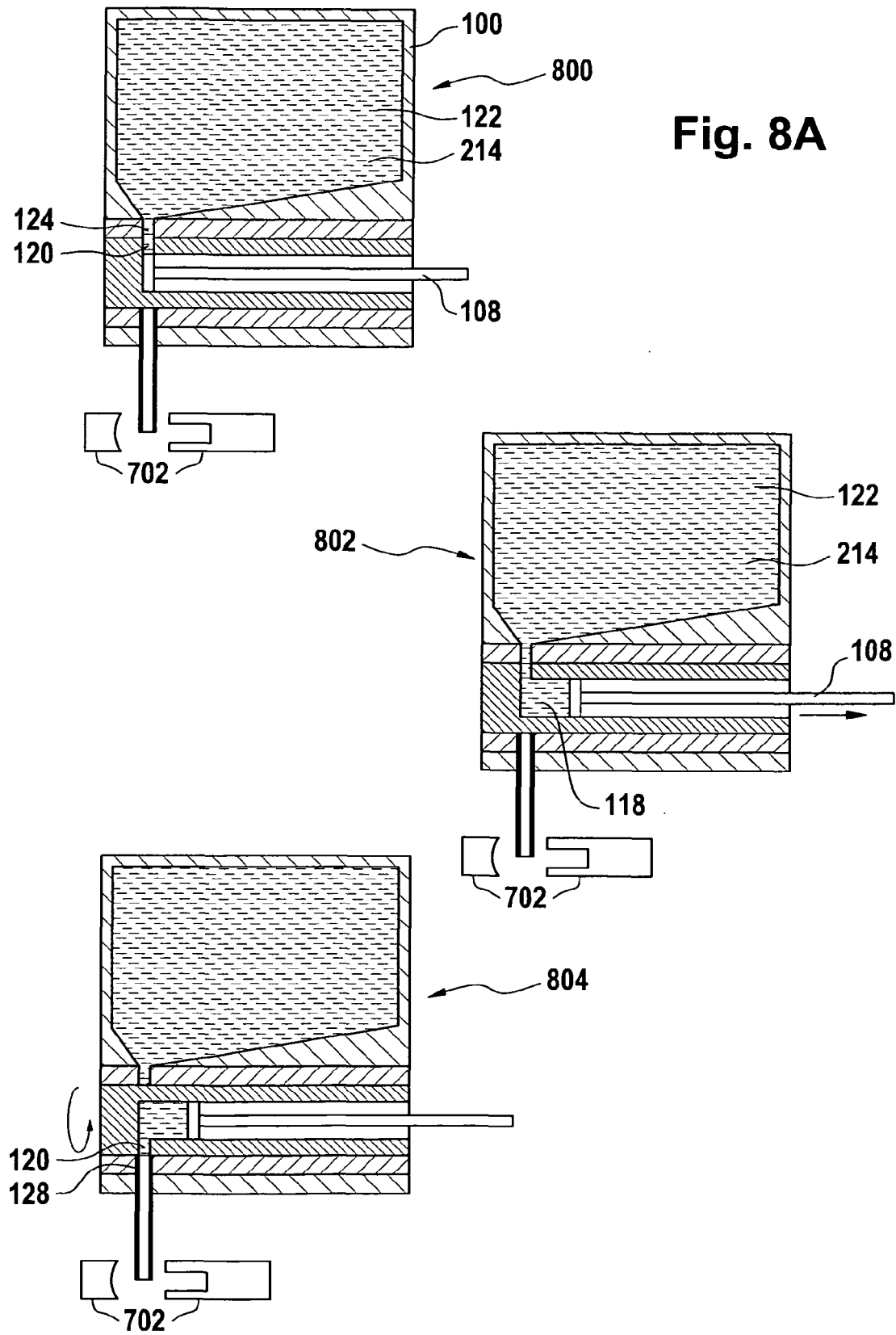
Figure 8B:
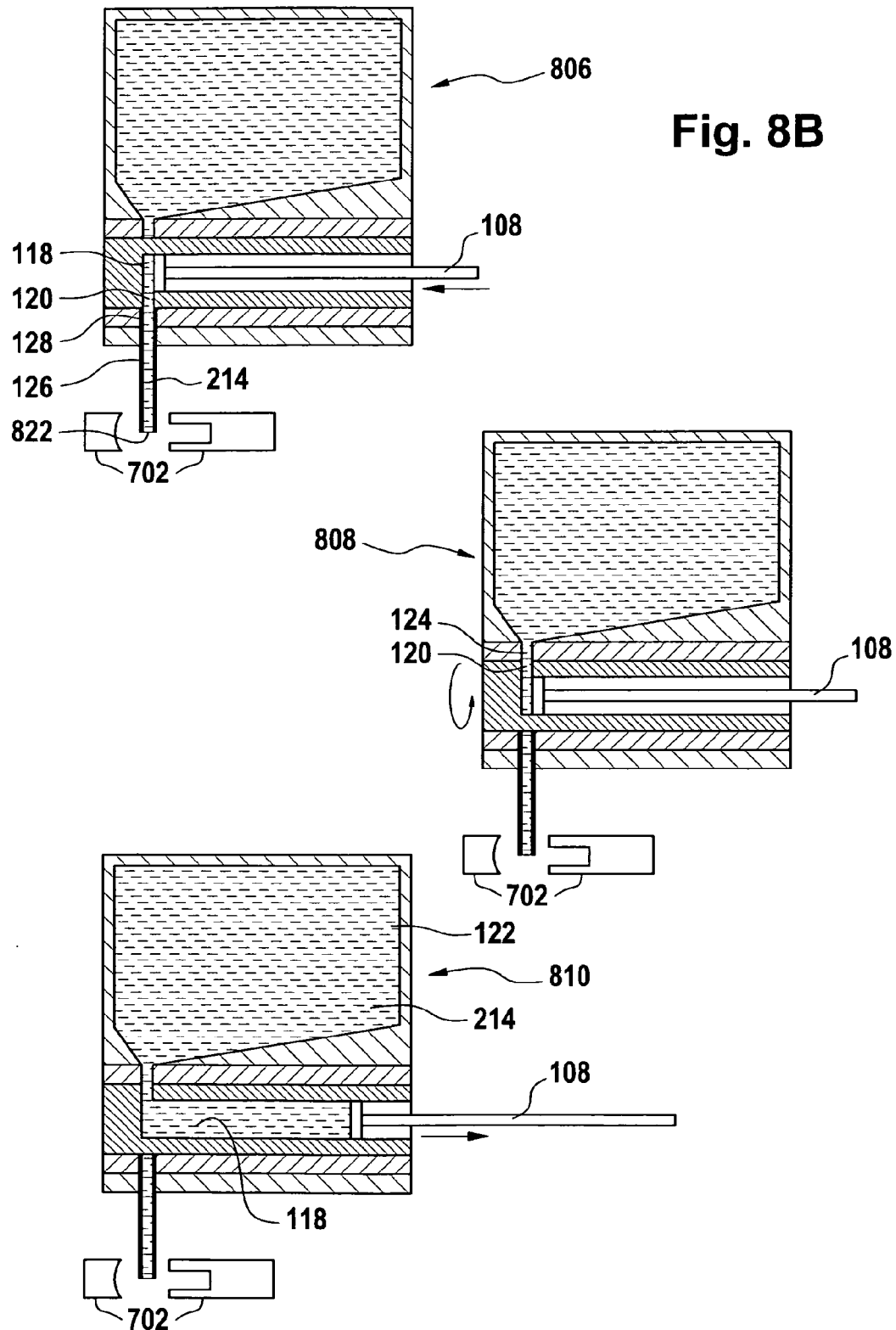
Figure 8C:
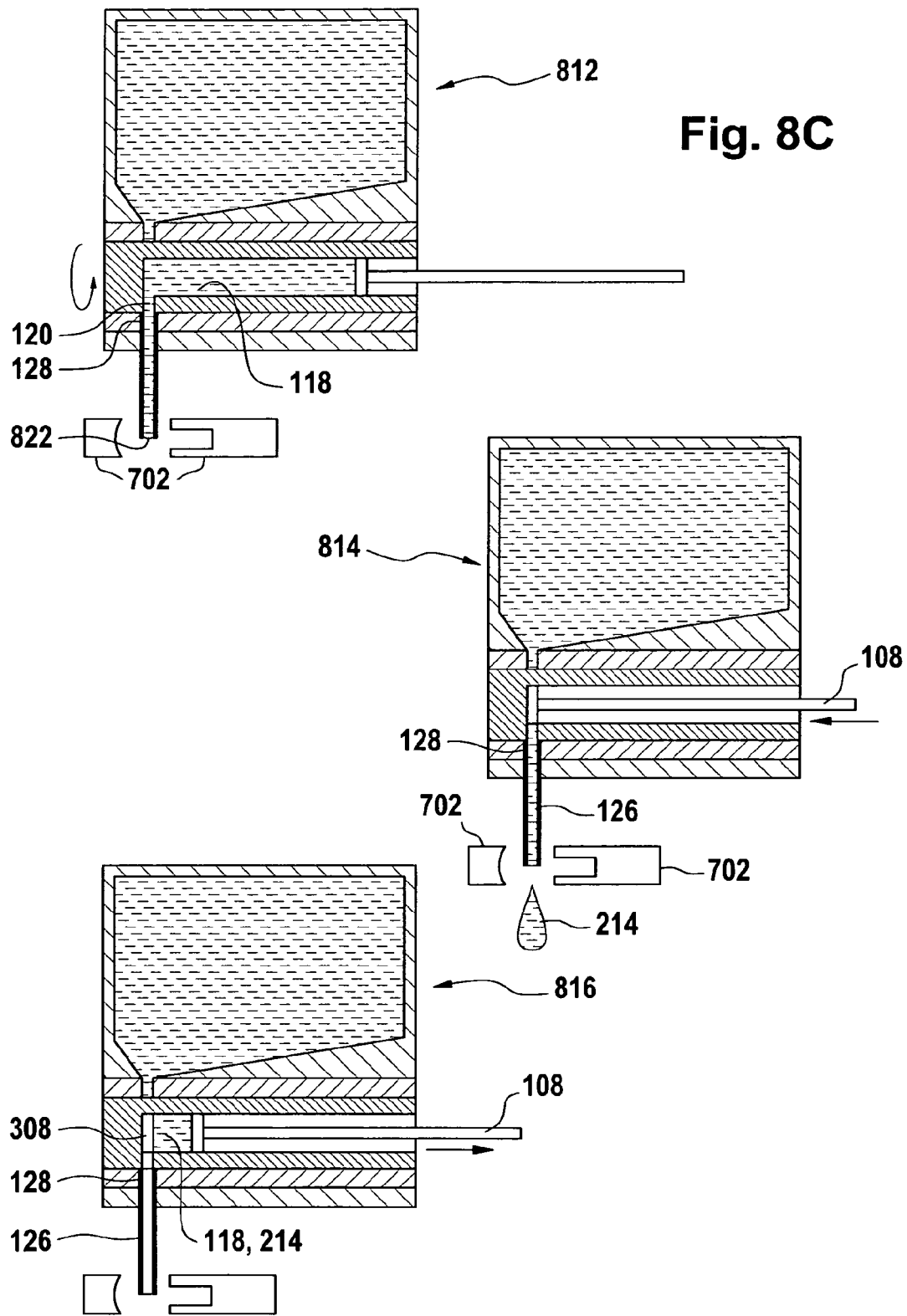

FIG. 8 shows 11 views 800, 802, 804, 806, 808, 810, 812, 814, 816, 818, 822 illustrates the functioning of a cartridge 100 in conjunction with a meniscus detector 702. In these examples, the meniscus detector 702 can be an optical sensor. The use of the optical sensor 702 is exemplary. Other types of sensors may also be used.

In view 800, the pumping chamber conduit 120 can be rotated into position such that it can be aligned with the reservoir conduit 124. The plunger 108 is shown in this view 800 as being fully depressed. The pumping chamber 118 can therefore be extremely small and is not visible in this view 800. The position of this plunger 108 in this position may not be necessarily required as long as the plunger 108 can still be able to increase or withdraw a reasonable amount of fluid 214 from the reservoir 122. Next in view 802, the plunger 108 can be withdrawn to increase the volume of the pumping chamber 118 and draw fluid 214 from the reservoir 122 into the pumping chamber 118. Next in view 804, the pumping chamber conduit 120 can be rotated into position such that can be it is aligned with the outlet conduit 128.

In view 806, the plunger 108 can be depressed which can decrease the volume of the pumping chamber 118. This can force fluid 214 into the outlet conduit 128 and the outlet nozzle 126. The plunger 108 can be controlled in accordance with the meniscus detector 702. When the meniscus 822 reached a predetermined position, the meniscus detector 702 can be used to detect this and the depression of the plunger 108 can be halted. Next in view 808, the pumping chamber conduit 120 can again be rotated into alignment with the reservoir conduit 124. In view 810, the plunger 108 can be withdrawn thereby increasing the volume of the pumping chamber 118 and drying fluid 214 from the reservoir 122. Next in view 812, the pumping chamber conduit 120 can be rotated into position so that it can be aligned with the outlet conduit 128. The pumping chamber 118 can be filled with the fluid and the meniscus 22 can be in the predetermined location. Next in view 814, the plunger 108 can be depressed forcing fluid out of the outlet nozzle 126. It can be seen in view 814 that there can still be fluid within the outlet conduit 128 and the outlet nozzle 126. Next in view 816, the plunger 108 can be retracted to withdraw the fluid 214 that can be in the outlet conduit 128 and the outlet nozzle 126 back in two the pumping chamber 118. In view 818, the pumping chamber conduit 120 can be rotated into position with the reservoir conduit 124. Then finally in view 820, the plunger 108 can be depressed forcing the fluid back into the reservoir 122. A bubble 308 which can be inside the pumping chamber can be forced out of the pumping chamber and into the reservoir 122.

Figure 9:
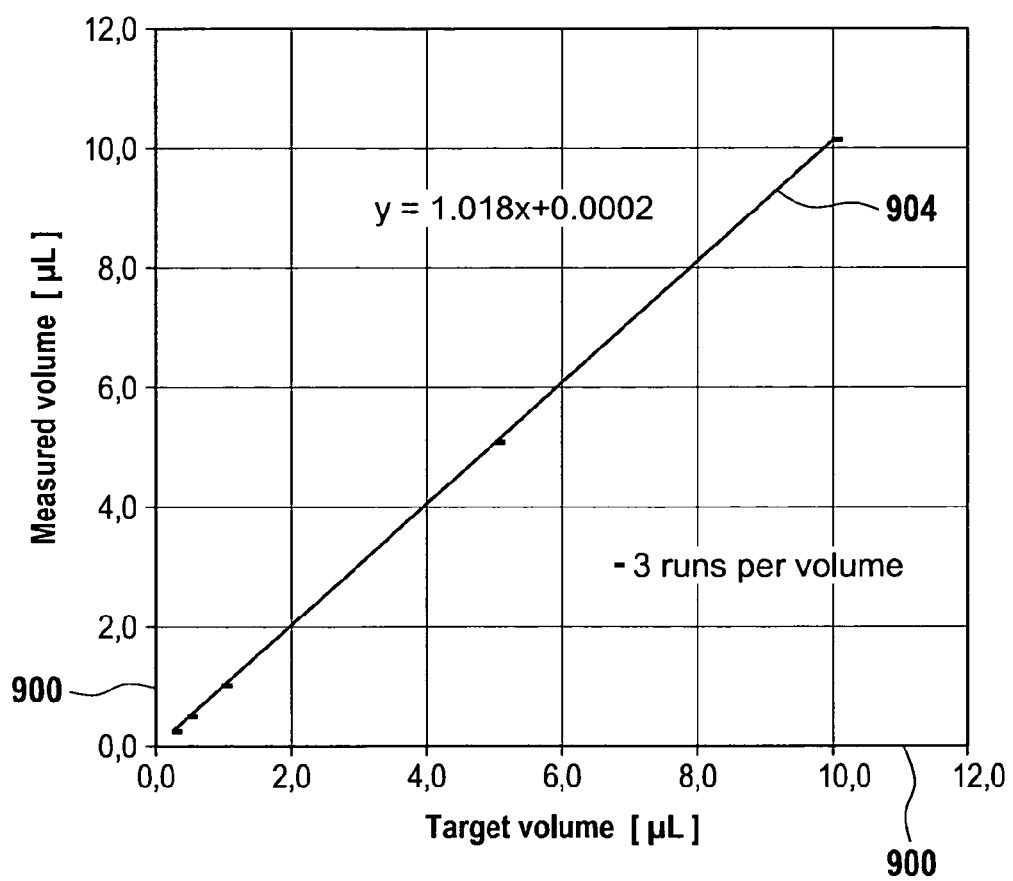
FIG. 9 illustrates the correlation of the target volume and measured volume for an embodiment of a rotary valve according to an embodiment of the present disclosure.

FIG. 9 illustrates the correlation of the target volume and measured volume for an embodiment of a rotary valve comprising a pumping chamber volume of 10 μL. FIG. 9 shows a plot of the target volume (in μL) 900 vs the measured volume (in μL) 902. The measured points are connected by a linear fit indicated by the dashed line 904. For each data point, water was used as the test fluid. The measured volume has been determined using a calibrated scale. Each data point can indicate an average of three trials performed for the same target volume. In each trial or run, the pumping was repeated 24 times. In other words, at each target volume three trials or runs were performed. For each of these three runs, the fluid was dispensed 24 times and averaged. The data shown in FIG. 9 illustrate both the very high accuracy (small error bars, even for very small target volumes) and linearity (linear fit is very close to the ideal bisector line) over a large range of target volumes which can be achieved by using an rotary valve according to the invention.

Figure 10:
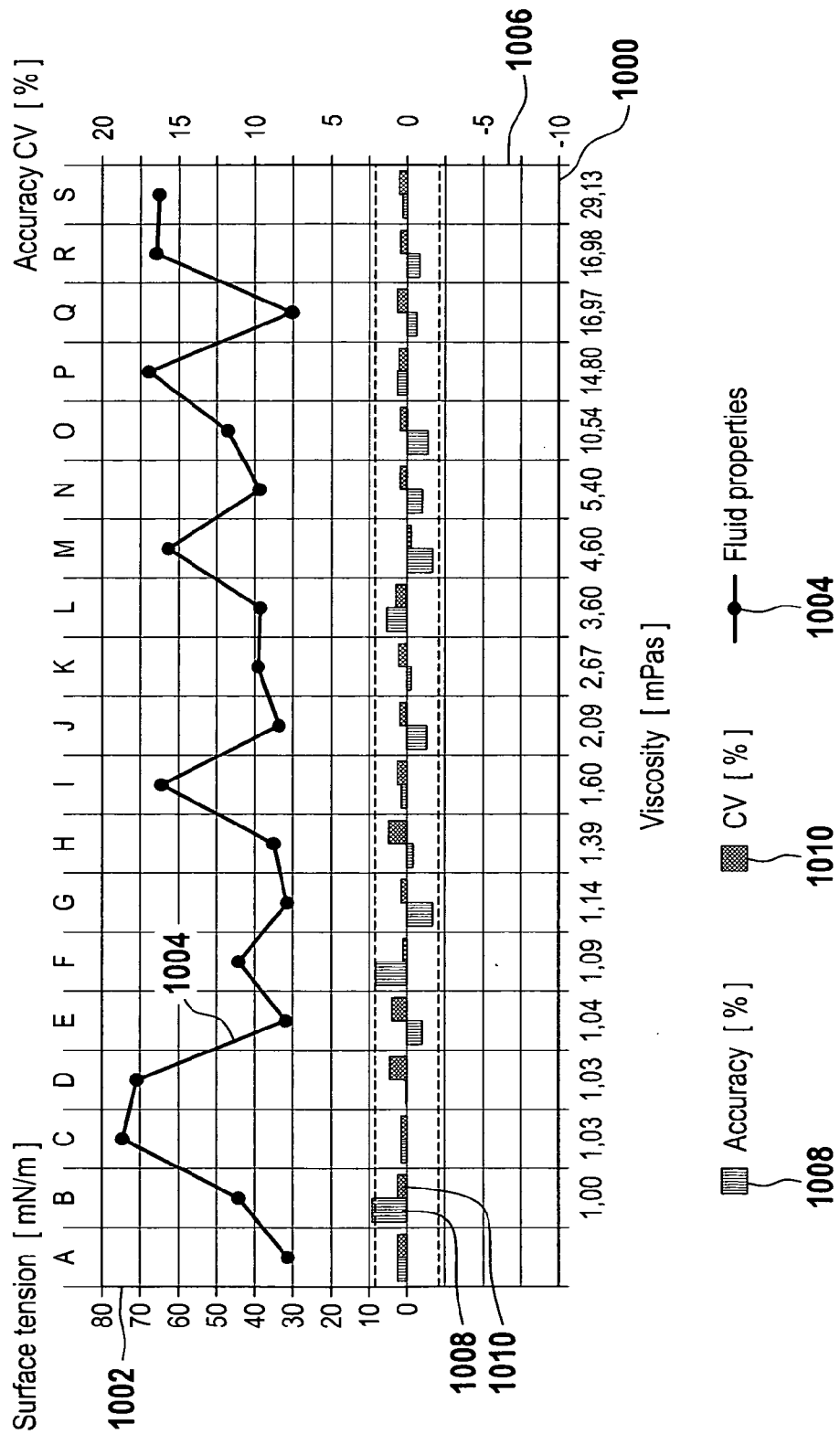
FIG. 10 illustrates a plot indicating the accuracy and the coefficient of variation for the dispensing of fluids of different viscosities and surface tensions by a rotary valve according to an embodiment of the present disclosure.

FIG. 10 shows a plot indicating the accuracy and the coefficient of variation (CV) for the dispensing of fluids by an embodiment of a rotary valve comprising a pumping chamber volume of 10 μL for fluids of different viscosities and surface tensions. The X-axis 1000 indicates the viscosity of 19 different fluids A-S in terms of mPas. The left Y-axis 1002 indicates the surface tension of each of these fluids in terms of mN/m. The plot of viscosity vs. surface tension for each fluid is indicated by the line 1004. The measured volume has been determined using a calibrated scale. For each fluid, a trial comprising 21 subsequent dispenses of a target volume of 1 μL has been performed.

The right Y-axis 1006 indicates the accuracy of the dispensing 1008 (left column, in %) and the coefficient of variation 1010 (right column, in %) for each fluid.

The data shown in FIG. 10 illustrate that the accuracy and reproducibility of dispensing which can be achieved by using an rotary valve according to the invention is very high and (almost) independent of the viscosity and/or surface tension of the fluid which is dispensed: If comparing the accuracy and CV values of the different fluids A-S in consideration of their increasing viscosity (indicated on the X-axis), no effect of the viscosity both on accuracy and CV can be identified. Also, if comparing the accuracy and CV values of the different fluids A-S in consideration of their respective surface tension (shown in 1004 and indicated on the left Y-axis), also no effect of the surface tension both on accuracy and CV can be identified.

Figure 11:
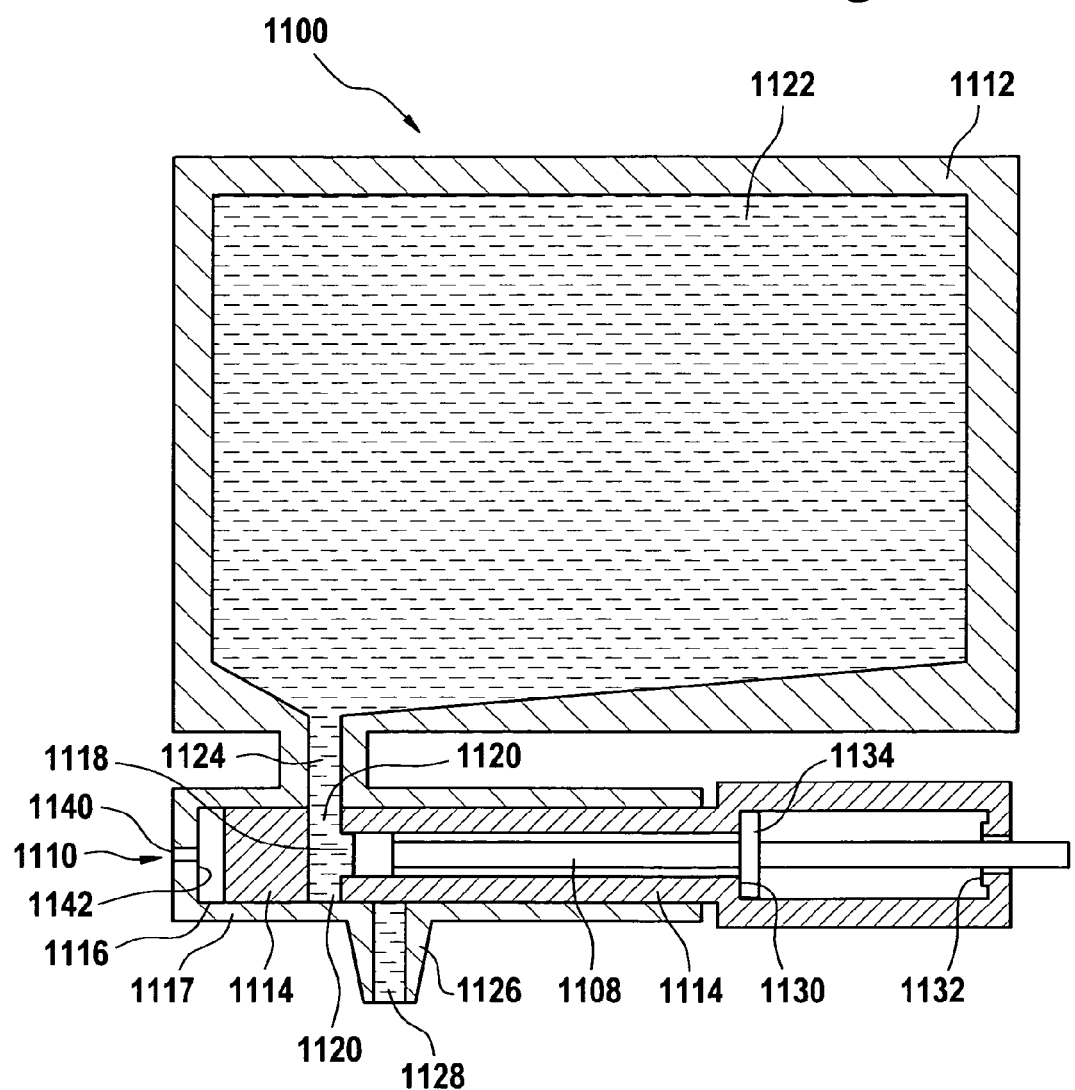
FIG. 11 illustrates a cartridge according to an embodiment of the present disclosure.

FIG. 11 shows a cartridge 1100. The cartridge can comprise a plunger 1108 which can slide within a piston 1114. The piston 1114 and a volume 1116 can form a slide valve 1110. The volume 1116 may be formed in a housing 1117 or a portion of the cartridge 1100. The slide valve 1110 can be capable of rectilinear motion. As the piston moves 1114, there can be a pumping chamber conduit 1120 that can be moved along with the piston 1114. There can be a hole within the piston 1114 that the plunger 1108 can move in. This hole in the piston 1114 and the plunger 1108 can form a pumping volume 1118.

The piston 1114 can move the pumping chamber conduit 1120 into different locations. In this view, it is shown as aligned with a reservoir conduit 1124. The reservoir conduit 1124 can connect a reservoir 1122 filled with a fluid with the pumping chamber 1118. The reservoir 1122 can be surrounded by a cartridge body 1112. In this position, the plunger 1134 can be moved such as to increase or decrease the volume of the pumping chamber 1118. When the plunger 1108 is moved to increase the volume of the pumping chamber 1118 when the piston 1114 is in this location, fluid can be withdrawn from the reservoir 1122.

The piston 1114 can be moved such that the pumping chamber conduit 1120 can be aligned with an outlet conduit 1128. The outlet conduit 1128 can provide access to an outlet nozzle 1126. When the pumping chamber conduit 1120 is aligned with the outlet conduit 1128, the fluid can be expelled from the pumping chamber 1118 through the nozzle 1126 by decreasing the volume of the pumping chamber 1118.

In this embodiment, the piston 1114 is shown as having a first plunger mechanical stop 1130 and a second plunger mechanical stop 1132. The plunger in this example can have a mechanical extension 1134 that can contact the first plunger mechanical stop or the second plunger mechanical stop. In this embodiment, the entire pumping arrangement may be done only be actuating the plunger 1108. When the mechanical extension 1134 contacts the first plunger mechanical stop 1130, the plunger 1108 can push the piston 1114 such that the pumping chamber conduit 1120 can be aligned with the reservoir conduit 1124. When the mechanical extension 1134 contacts the second plunger mechanical stop 1132, the plunger 1108 can move the piston 1114 such that the pumping chamber conduit 1120 can be aligned with the outlet conduit 1128.

The first plunger mechanical stop 1130, the second plunger mechanical stop 1132 and the mechanical extension of the plunger 1134 may not be present in all embodiments.

In an alternative embodiment, the cartridge may have a reservoir mechanical stop. The reservoir mechanical stop can contact a contacting surface. This can provide a reservoir mechanical stop that can roughly align the pumping chamber conduit 1120 with the reservoir conduit 1124. In some embodiments, there may also be an outlet mechanical stop present and corresponding contacting surface for aligning the pumping chamber conduit with the outlet conduit.

In an alternative embodiment, an end of the volume 1116 may provide a mechanical stop for aligning the pumping chamber conduit 1120 with the reservoir conduit. For instance, in this example, the volume 1116 can be closed at one end with the exception of an air vent 1140. The ending surface 1142 may be used in some embodiments as a mechanical stop for the piston 1114 also.

In some embodiments, the plunger 1134 may operate in the position of the piston 1114 without the use of the reservoir mechanical stop or even a conduit mechanical stop. For instance, the surface between the piston 1114 and the volume 1116 may be constructed such that it can be more difficult to move piston 1114 than it can be for the plunger 1108, e.g., because the static friction between the piston 1114 and the volume 1116 can be larger than the static friction between the plunger 1108 and the corresponding hole in the piston 1114. In this case, the plunger 1108 can be moved without dislocating the piston 1114 unless the plunger 1108 contacts one of the first plunger mechanical stop 1130 or the second plunger mechanical stop 1132.

FIG. 12 shows the cartridge 1100 of FIG. 11 connected to an actuator assembly 1200. The actuator assembly 1200 can comprise a linear actuator 1202 which can move along a linear track 1204 in the direction 1206. The linear actuator 1202 can be connected by a coupling assembly 1208 to the plunger 1108.

Figure 13A:
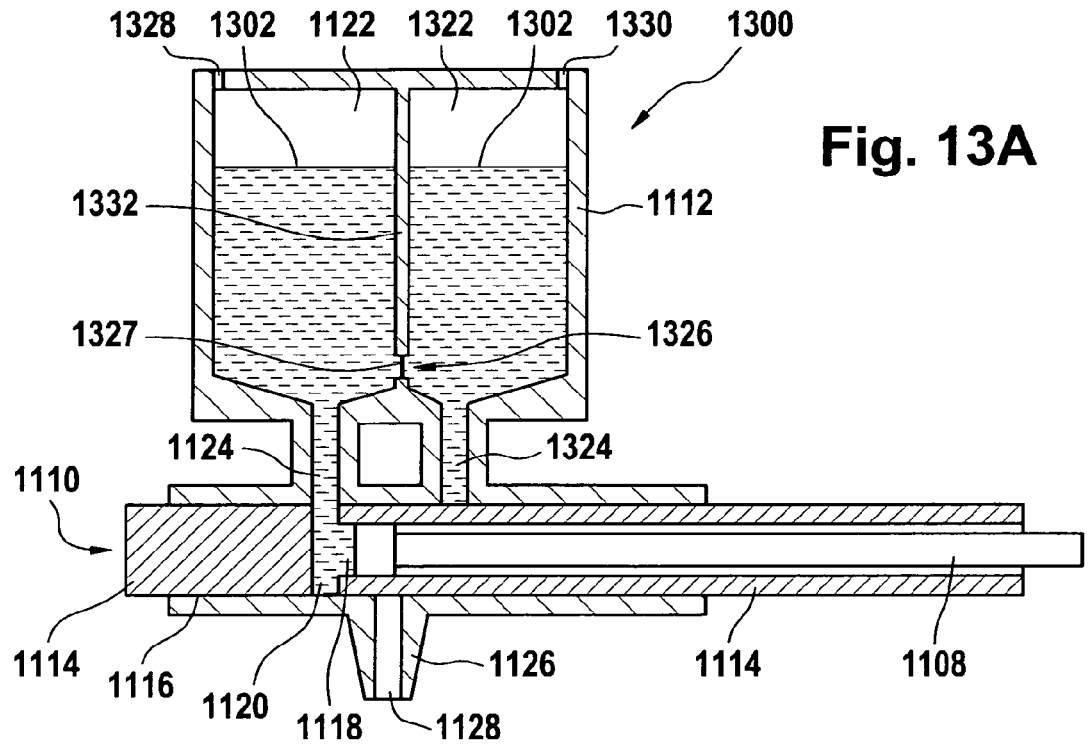
FIG. 13A illustrates a cartridge according to another embodiment of the present disclosure.

FIG. 13A shows a further example of a cartridge 1300. The example in FIG. 13 is similar to that shown in FIGS. 11 and 12 with several additional features. In this embodiment, there can be a secondary reservoir 1322. The secondary reservoir 1322 can be connected to a secondary reservoir conduit 1324 which can be aligned with the pumping chamber conduit 1120. There can be an optional connection for a connecting conduit 1326 between the reservoir 1122 and the secondary reservoir 1322. In this example, there can also be an optional membrane 1327 covering the surface of the connecting conduit 1326. The membrane 1327, for instance, may prevent bubbles from the secondary reservoir 1322 from entering the reservoir 1122. This structure may, for instance, be useful for pumping fluid 1302 out of the reservoir 1122 and returning unused fluid 1302 to the secondary reservoir 1322. The reservoir 1122 can have an optional vent 1328 and the secondary reservoir 1322 can have an optional vent 1330. There can be a side wall 1332 which can divide the reservoir 1122 from the secondary reservoir 1322. In some embodiments, this dividing wall 1332 may not be present in which case the primary reservoir can form a first portion of the reservoir and the secondary reservoir 1322 can form a second portion of the reservoir. In this example, the plunger 1108 and the piston 1114 can be actuated independently. Such a structure for the plunger 1108 and the piston 1114 may also be used as an alternative to the structure shown in FIG. 11.

Figure 13B:
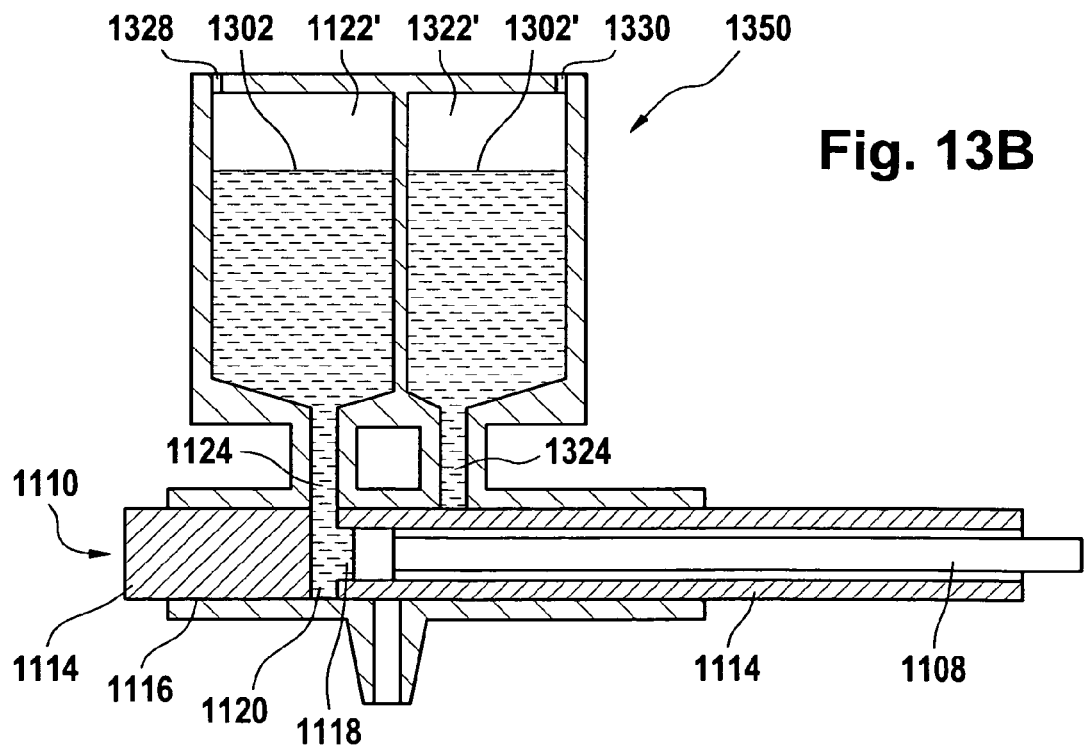
FIG. 13B illustrates a cartridge according to yet another embodiment of the present disclosure.

FIG. 13B shows an alternative example of a cartridge 1350 that is similar to the cartridge 1300 shown in FIG. 13A. In the embodiment of FIG. 13B, there can be a separate reservoir 1122' and a separate secondary reservoir 1322'. The connecting conduit 1326 of FIG. 13A is not present. The reservoir 1122' may contain a first fluid 1302 and the secondary reservoir 1322' may contain a second fluid 1302'. The first fluid 1302 and the second fluid 1322' may be different fluids.

FIG. 14 shows the cartridge 1300 in FIG. 13 connected to an actuator assembly 1400. In this embodiment, both the plunger 1108 and the piston 1114 can be actuated independently. There can be a linear actuator 1202 which can move along a linear track 1204 which can be connected to the plunger 1108 by a coupling assembly 1208. There can be a linear actuator 1402 which can move along linear track 1404 which can be connected to the piston 1114 by a coupling assembly 1408. Both linear actuators 1202 and 1402 can move in the direction 1206. The actual implementation of the actuator assembly 1400 is intended to be representative and other actual constructions may be used also.

FIGS. 15A and 15B show five different views 1500, 1502, 1504, 1506, 1508 of the slide valve 1110 with a plunger 1108 and piston 1114 of the embodiment shown in FIG. 11. FIGS. 15A and 15B show an example of how the piston 1114 and plunger 1108 can be used to pump fluid from the reservoir chamber through the outlet nozzle 1126. In view 1500, the pumping chamber conduit 1120 can be aligned with the reservoir conduit 1124. The pumping chamber volume 1118 can be at its minimum volume. The mechanical extension 1134 can be in contact with the first plunger mechanical stop 1130. Next in view 1502, the plunger 1108 can be withdrawn in direction 1510. The plunger can be withdrawn until the mechanical extension 1134 contacts the second plunger mechanical stop 1132. In this embodiment, the piston 1114 can require more force to move than the plunger 1108. In other words, the plunger 1108 can slide easier than the piston 1114. This can be accomplished by designing the plunger 1108 so that it can have less friction than the piston 1114. This can enable the piston 1114 and the plunger 1108 to use a single actuator. Mechanical stops 1130 and 1132 can be used to restrict the motion of the plunger 1108. The frictional force on the plunger can cause the plunger 1108 to move first when a linear force is applied to the plunger 1108. When the plunger 1108 hits a mechanical stop 1130, 1132, then the plunger 1108 and the piston 1114 can move together.

The pumping chamber 1118 can be filled with fluid from the fluid reservoir. Next in view 1504, the plunger 1108 can be withdrawn further. The mechanical extension 1134 can be in contact with the second plunger mechanical stop 1132 so the plunger 1108 can exert force on the piston 1114. The plunger 1108 can be moved so far such that the piston 1114 can move the pumping chamber conduit 1120 into alignment with the outlet conduit 1128. Next in view 1506, the plunger 1108 can be moved in direction 1514. The fluid can be forced out of the pumping chamber 1118 by the plunger 1108 and through the outlet conduit 1128. Fluid can exit the outlet nozzle 1126 and can form droplets 1516 exiting the cartridge through the outlet nozzle 1126.

Finally, in view 1508, the plunger 1108 can be depressed 1516 further such that the mechanical extension 1134 can exert force on the second plunger mechanical stop 1132 to force the piston 1114 to align the pumping chamber conduit 1120 with the reservoir conduit 1124 again. In this embodiment, there can be no mechanical stop to align the piston with the reservoir conduit 1124. This can most likely be performed by controlling the actuator of the plunger 1108. View 1508 is substantially the same as view 1500. In this position, the pumping process can begin again.

FIGS. 16A and 16B illustrate an alternative embodiment to the slide valve 1110 of FIG. 11. In the embodiment shown in FIGS. 16A and 16B, the slide valve can comprise a piston 1114 with a plunger 1108. The operation of this alternative embodiment is also illustrated in FIGS. 16A and 16B by views 1600, 1602, 1604, 1606, and 1608. In the embodiment shown in FIGS. 16A and 16B, the linear position of the reservoir conduit 1124 and the outlet conduit 1128 can be reversed with respect to those in FIGS. 15A and 15B. In contrast to the embodiment shown in FIGS. 15A and 15B, the piston 1114 can require less force to move than the plunger 1108. In other words, the piston 1114 can slide easier than the plunger 1108. This can be accomplished by designing the plunger 1108 so that it can have more friction than the piston 1114. As is described below, the mechanical stops 1130, 1132, 1609 and 1610 in combination with the frictional plunger 1108 can enable pumping to be accomplished with a single actuator.

This embodiment can have an outlet mechanical stop 1610 that can align the piston 1114 such that the pumping chamber conduit 1120 can align with the outlet conduit 1128. This embodiment can also have a reservoir mechanical stop 1609 that is shown as extending out from the slide valve 1110. The piston can have a contacting surface 1611. When the contacting surface 1611 contacts the reservoir mechanical stop 1609, the reservoir conduit 1124 can be aligned with the pumping chamber outlet 1120. There can also be an outlet mechanical stop 1610 on the slide valve 1110 that can be operable for becoming in contact with contacting surface 1613. When the outlet mechanical stop 1610 contacts contacting surface 1613, the pumping chamber conduit 1120 can be aligned with the with the outlet conduit 1128.

In view 1600, the pumping chamber conduit 1120 can be aligned with the reservoir conduit 1124. The pumping chamber 1118 can be at its minimum and the contacting surface 1611 of the piston 1114 can be in contact with the reservoir mechanical stop 1609. The slide valve 1110 is shown as having a first plunger mechanical stop 1130 and a second plunger mechanical stop 1132. When mechanical extension 1134 is in contact with the first plunger mechanical stop 1130, then the volume of the pumping chamber 1118 can be at a minimum. When the mechanical extension 1134 is in contact with the second plunger mechanical stop 1132, then the volume of the pumping chamber 1118 can be at a maximum.

The piston 1108 can have its mechanical extension 1134 in contact with the first plunger mechanical stop 1130. Next in view 1602, the plunger 1108 can be withdrawn in direction 1612. The volume of the pumping chamber 1118 can increase and fluid can be withdrawn from the reservoir chamber until the mechanical extension 1134 contacts the second plunger mechanical stop 1132. The reservoir mechanical stop 1609 can prevent the piston 1114 from moving during this.

Next in view 1604, the piston 1108 can be moved in direction 1614. The volume of the pumping chamber 1118 can stay the same and the contacting surface 1613 of the piston 1114 can come in contact with the outlet mechanical stop 1610. This can align the pumping chamber conduit 1120 with the outlet conduit 1128.

Next in step 1606, the plunger 1108 can be depressed further until the mechanical extension 1134 contacts the first plunger mechanical stop. The piston 1114 can already be in contact with the outlet pumping chamber conduit mechanical stop 1610. As the plunger 1108 is depressed in direction 1616, the piston 1114 cannot move any further. The plunger 1108 can then force fluid out of the pumping chamber 1118 through the outlet conduit 1128 and the nozzle 1126. Droplets of fluid 1516 can form exiting the cartridge. The plunger 1108 can be depressed until the mechanical extension 1134 comes in contact with the first plunger mechanical stop 1130.

Next in step 1608, the plunger 1108 can be moved in direction 1618. The plunger can be moved in direction 1618 until the contacting surface 1611 of the piston 1114 contacts the reservoir mechanical stop 1609. The piston 1114 and plunger 1108 can now be in the same position they were in view 1600. The pumping cycle has been completed. This process may be repeated to pump more fluid 1516 out of the cartridge.

FIG. 17 shows two views 1700, 1702 of a slide valve 1110 and plunger combination 1108 that can be an alternative to that shown in FIG. 11. In this embodiment, there can be no mechanical stops and the piston 1114 and the plunger 1108 may be operated independently. In view 1700, the piston 1114 can be moved such that the pumping chamber conduit 1120 can be in alignment with the reservoir conduit 1124. Fluid may be pumped into the pumping chamber 1118 by moving the plunger 1108 outwards. Fluid may also be moved back into the reservoir conduit 1124. For instance, used fluid may be moved back into the reservoir chamber 1124 or the plunger 1108 may be moved in a reciprocating fashion to mix the fluid. View 1702 shows the piston 1114 in a different position such that the pumping chamber conduit 1120 can be in alignment with the outlet conduit 1128. The piston 1108 can be moved in the direction 1704 to pump fluid through the outlet conduit 1128 and the outlet nozzle 1126 thus forcing droplets 1516 of fluid out of the cartridge.

FIGS. 18A and 18B illustrate one way of operating the slide valve 1110 of the embodiment shown in FIG. 13. The method illustrated in FIGS. 18A and 18B illustrate how the amount of fluid waste may be reduced during operation. This method is illustrated in eight different views, 1800, 1802, 1804, 1806, 1808, 1810, 1812, and 1814. The piston 1114 and plunger 1108 can be operated independently. The method can start in view 1800. In view 1800, the pumping chamber conduit 1120 can be aligned with the reservoir conduit 1124. The plunger 1108 can be in a position where the pumping chamber 1118 can have a relatively small volume. In view 1802, the plunger 1108 can be withdrawn in direction 1816. This can cause fluid to be drawn from the fluid reservoir into the pumping chamber 1118. Next in view 1804, both the plunger 1816 and the piston 1818 can both be withdrawn simultaneously in direction 1820, 1818. The piston 1114 and the plunger 1108 can both be moved the same amount. They can both be moved until the pumping chamber conduit 1120 is aligned with the outlet conduit 1128.

Next in view 1806, the piston 1114 can remain in the same position and the plunger 1108 can be depressed 1822. This can force the fluid out of the pumping chamber 1118 and through the outlet conduit 1128. This can force the fluid in droplets 1516 out of the outlet nozzle 1126.

Next in view 1808, to remove fluid remaining within the outlet conduit 1128, the plunger 1108 can be withdrawn in direction 1824 with the piston 1114 remaining in the same position. The plunger 1108 can be withdrawn 1824 sufficiently such that the majority of fluid can be removed from the outlet conduit 1128. Also a quantity of air may be withdrawn also forming a bubble 1826. This can result in a complete emptying of the outlet conduit 1128 from remaining fluids and thereby can avoid the drying of fluid compounds within this outlet conduit 1128. Due to this complete emptying of the outlet conduit 1128, no washing or "priming" steps before the next dispensing step can be necessary resulting in a maximum efficiency of the use of the fluid volume within the reservoir. Thus far, the amount of fluid used for cleaning purposes can be reduced; however the presence of a bubble may cause inaccuracies in the dispensing of fluid.

Next in view 1810, to eliminate this problem both the piston 1114 and the plunger 1108 can simultaneously be withdrawn in direction 1830, 1832. Both the piston 1114 and the plunger 1108 can be moved the same amount. They can be moved such that the pumping chamber conduit 1120 can be aligned with the secondary reservoir conduit 1324.

Next in view 1812, the piston 1114 can remain stationary and the plunger 1108 can be depressed in direction 1834. This can force the bubble 1826 to the secondary reservoir. This can remove the bubble 1826 from the pumping chamber 1118 and the pumping chamber conduit 1120. The bubble 1826 can no longer interfere with the proper metering of the fluid in the pumping chamber 1118.

Finally, in view 1814, both the piston 1114 and the plunger 1108 can be depressed simultaneously in direction 1836, 1838 the same amount. The pumping chamber outlet 1120 can again be aligned with the reservoir conduit 1124 and the pumping cycle can be complete. The pump may be used again without the bubble 1826 interfering with the correct measurement or metering of the fluid.

Figure 19:
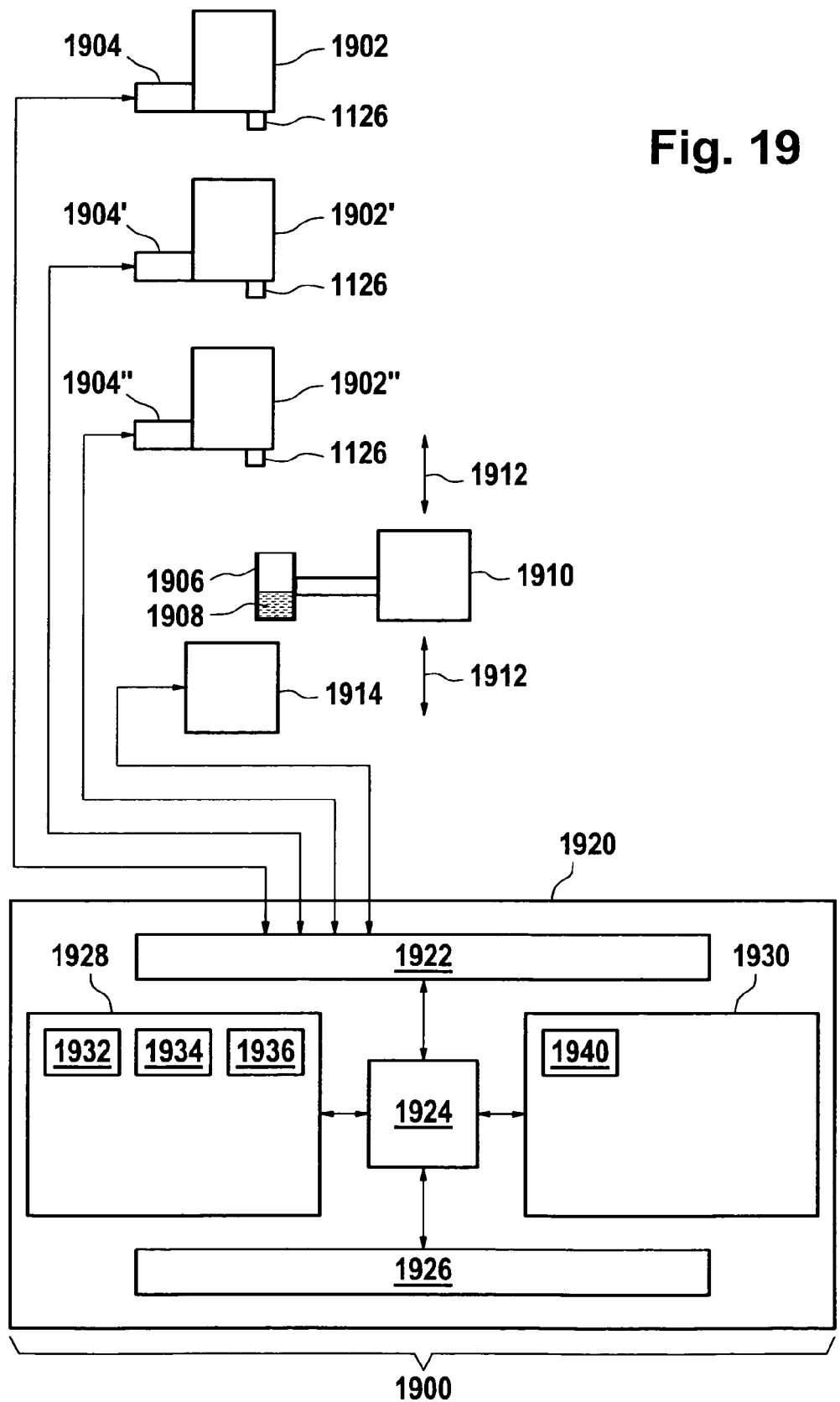
FIG. 19 illustrates an automatic analyzer according to an embodiment of the present disclosure.

FIG. 19 illustrates an automatic analyzer 1900. This automatic analyzer is shown as having three cartridges 1902, 1902' and 1902". There can be an actuator assembly 1904 connected to cartridge 1902. There can be an actuator assembly 1904' attached to cartridge 1902'. There can be an actuator assembly 1904" attached to cartridge 1902". The actuator assemblies 1904, 1904', 1904" can actuate the slide valve and plunger of the cartridges 1902, 1902', 1902". The automatic analyzer 1900 is shown as having a relative mover 1910 which can provide relative movement 1912 between a reagent container or cuvette 1906 and the cartridges 1902, 1902' and 1902". The reagent container or cuvette 1906 is shown as containing a biological sample 1508.

The cartridges 1902, 1902', 1902" may be used to add one or more fluids to the biological sample 1908. The automatic analyzer 1900 is shown as further containing a sensor system 1914. The sensor system can comprise one or more sensors for measuring a quantity or a physical or chemical or biochemical property of the biological sample 1908. For example, the sensor system 1914 may comprise an nuclear magnetic resonance (NMR) system, an optical transmission or reflectance measurement system, a pH meter, a camera system, a polymerase chain reaction (PCR) apparatus, a Electrochemiluminescence (ECL) apparatus, a spectroscopic measurement system, an electrochemical or an optical sensor, and a chromatography system. The relative mover 1910 can move the reagent container or cuvette 1906 to the sensor system 1914.

The arrangement of the cartridges 1902, 1902', 1902" and the sensor system 1914 is representative. In some embodiments, the reagent container or cuvette 1906 may remain in a fixed position and the cartridges 1902, 1902', 1902" may move. The actuation systems 1904, 1904', 1904" and the sensor system 1914 are shown as being connected to a hardware interface 1922 of a computer system 1920. The computer system 1920 can function as a controller for the automatic analyzer 1900. The computer 1920 is further shown as containing a processor 1924 which can control the operation and function of the automatic analyzer 1900 using the hardware interface 1922. The processor 1924 is shown as further being connected to a user interface 1926, computer storage 1928 and computer memory 1930. The computer storage 1928 is shown as containing an analysis request 1932. The analysis request 1932 can contain a request to analyze the biological sample 1908.

The computer storage 1928 is shown as further containing sensor data 1934 received from the sensor system 1914. The computer storage 1928 is shown as further containing an analysis result 1936 which can be determined using the sensor data 1934. The computer memory 1930 can contain a control module 1940. The control module 1940 can contain computer executable code which can enable the processor 1924 to control the operation and function of the automatic analyzer 1900. For instance, the control module 1940 may use the analysis request 1932 to generate commands to generate and send to the actuation systems 1904, 1904', 1904", the sensor system 1914 and the relative movement system 1910.

The control module 1940 may also generate the analysis result 1936 using the sensor data 1934.

Various algorithms may be used for controlling the dispensing of the fluid in different embodiments. For instance, the actuator assembly may be controlled by the processor to perform a series of predetermined actions to dispense the fluid. In another example, a sensor or metering system can be integrated into the automatic analyzer to measure the dispensing of the fluid. In this case, an algorithm can use the actuator assembly and the sensor to form a closed loop feedback to accurately control or meter the dispensing of the fluid.

Figure 20:
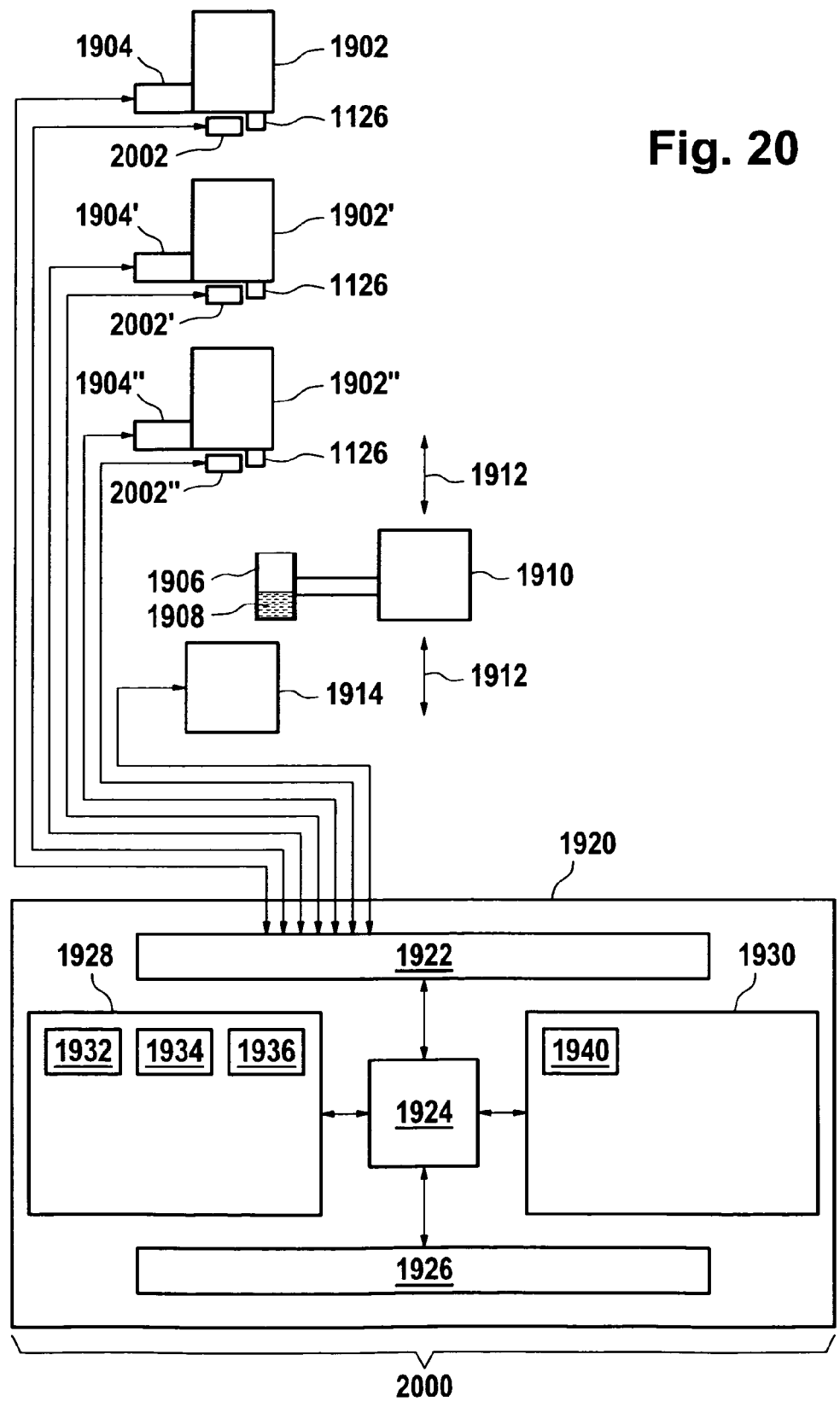
FIG. 20 illustrates an automatic analyzer according to another embodiment of the present disclosure.

FIG. 20 illustrates an automatic analyzer 2000 that is similar to the embodiment shown in FIG. 19. The automatic analyzer 2000 is similar to the automatic analyzer 1900 shown in FIG. 19. The automatic analyzer 2000 of FIG. 20 additionally can have a meniscus detector 2002, 2002', 2002". Each meniscus detector 2002, 2002', 2002" can be positioned adjacent to the outlet nozzle 1126. The meniscus detector 2002, 2002', 2002" can each be connected to the hardware interface 1922. This can enable the processor 1924 to control the actuator assemblies 1904, 1904', 1904" to control the location of the meniscus. This, for instance, may enable the processor to more accurately and/or reproducibly dispense fluid from the cartridges 1902, 1902', 1902".

Figure 21:
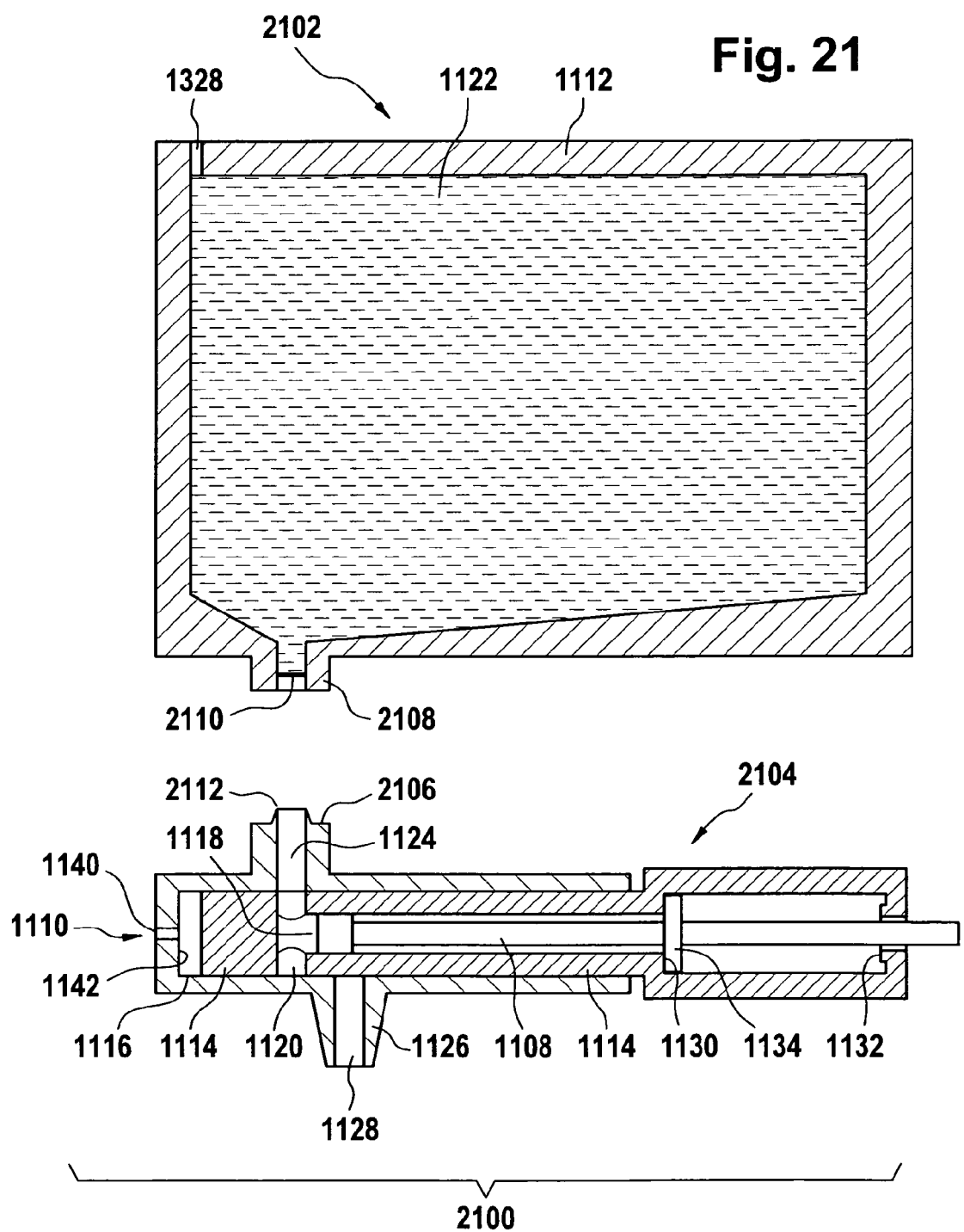
FIG. 21 illustrates a cartridge according to another embodiment of the present disclosure.

FIG. 21 shows a further example of a cartridge 2100. The cartridge 2100 shown in FIG. 21 is similar to that shown in FIG. 11. The cartridge 2100 shown in FIG. 21 can comprise two parts. There can be a attachable reservoir 2102 and a pumping unit 2104. The pumping unit 2104 can have a first connection 2106 and the attachable reservoir 2102 can have a second connection 2108. The first connection 2106 can connect to the second connection 2108. This can attach the attachable reservoir 2102 to the pumping unit 2104. The attachable reservoir 2102 in this example is shown as having a vent 1328. Near the second attachment 2108, the reservoir 1122 can be sealed with a seal 2110. Near the first connection 2106, there can be a knife edge 2112 that can open the seal 2110 when the first connection 2106 can be connected to the second connection 2108.

The embodiment shown in FIG. 21 can enable more flexibility and economy in preparing multiple cartridges. For instance, the volume of the attachable reservoir can be varied as well as the type of fluid filling the reservoir 1122. The pumping unit 2104 may also be varied. For instance, the diameter of the plunger 2108 as well as its stroke can be varied. This may allow for either a more accurate or a high-volume pumping unit to be selected.

FIGS. 22 through 25 show various embodiments of the slide valve 1110. All of the embodiments shown in FIGS. 22 through 25 show a plunger 1108 with a mechanical extension 1134 on the plunger. The piston 1114 in each of these embodiments can have a first plunger mechanical stop 1130 and a second the plunger mechanical stop 1132 as is described in FIG. 11.

Figure 22:
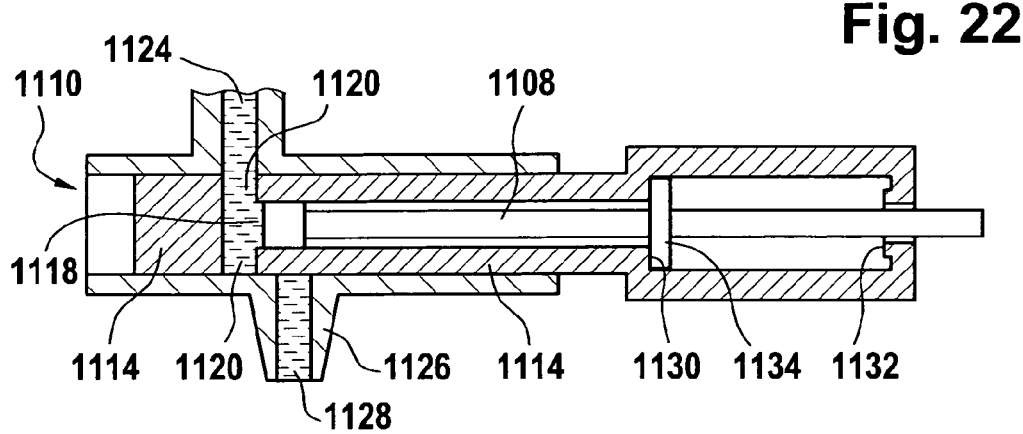
FIG. 22 illustrates an alternative slide valve design according to an embodiment of the present disclosure.

The embodiment of the slide valve 1110 shown in FIG. 22 may not have air vent 1140. There can also be no reservoir mechanical stop or outlet mechanical stop. Precise alignment of the pumping chamber conduit 1120 with the reservoir conduit 1124 or outlet conduit 1128 may be done or provided by an actuator.

Figure 23:
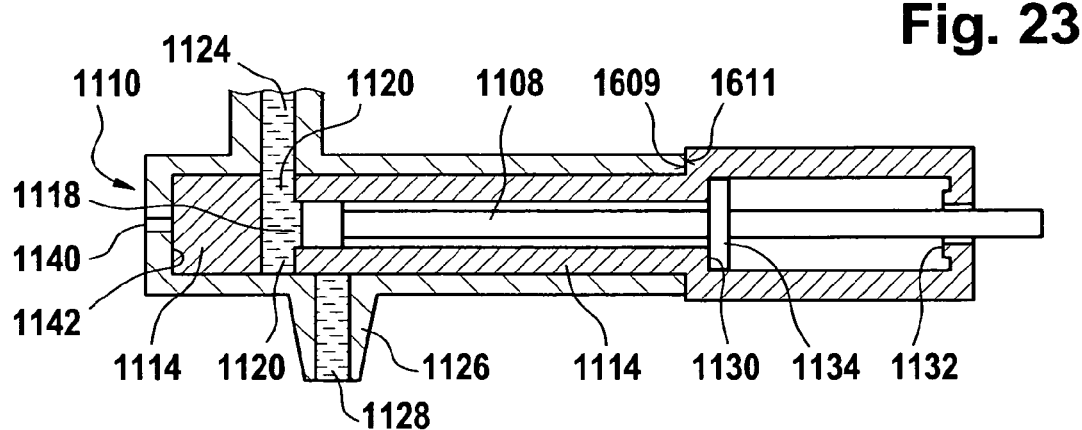
FIG. 23 illustrates an alternative slide valve design according to an embodiment of the present disclosure.

In FIG. 23, the slide valve 1110 is shown as comprising an air vent 1140 as is shown in FIG. 11. The slide valve 1110 is shown as comprising a reservoir mechanical stop 1609 for contacting a surface 1611 of the piston 1114. The reservoir mechanical stop 1609 can align the pumping chamber conduit 1120 with the reservoir conduit 1124. However, there can be no mechanical stop which can align the outlet conduit 1128 with the pumping chamber conduit 1120. Precise alignment of the pumping chamber conduit 1122 the outlet conduit 1128 may be done by a linear actuator.

Figure 24:
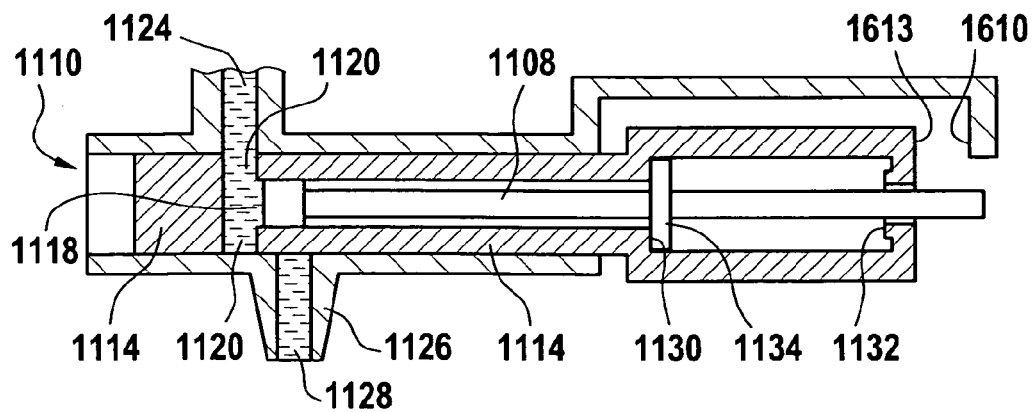
FIG. 24 illustrates an alternative slide valve design according to an embodiment of the present disclosure.

In FIG. 24, an air vent is not shown. In FIG. 24, the slide valve 1110 can comprise an outlet mechanical stop 1610 for contacting a surface 1613 of the piston 1114. The outlet mechanical stop 1610 can align the outlet conduit 1128 with the pumping chamber conduit 1120. However, there can be no mechanical stop for aligning the pumping chamber conduit 1120 with the reservoir conduit 1124. Precise alignment of the reservoir conduit may be provided by a linear actuator.

Figure 25:
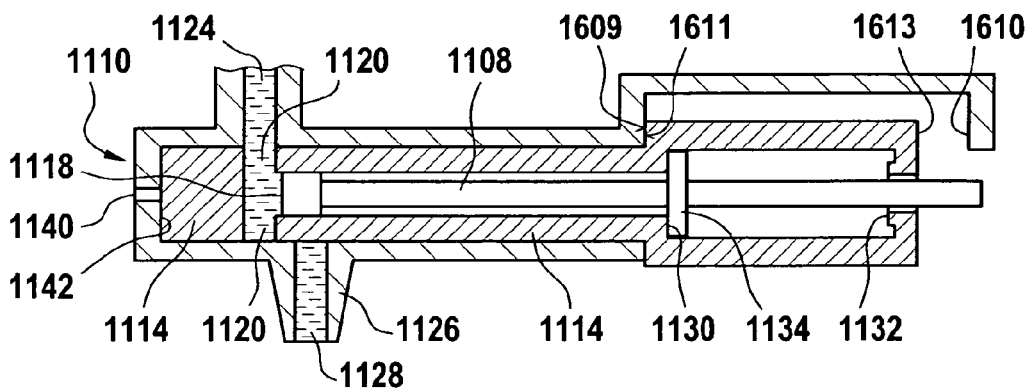
FIG. 25 illustrates an alternative slide valve design according to an embodiment of the present disclosure.

In FIG. 25, an air vent 1140 is shown. The embodiment shown in FIG. 25 can comprise a reservoir mechanical stop 1609 for contacting a surface 1611 of the piston 1114. The reservoir mechanical stop 1609 can align the pumping chamber conduit 1120 with the reservoir conduit 1124. The embodiment shown in FIG. 25 also shows an outlet mechanical stop 1610 on the slide valve 1110. The outlet mechanical stop 1610 can contact the cut surface 1613 of the piston 1114. The outlet mechanical stop 1610 can align the pumping chamber conduit 1120 with the outlet conduit 1128.

The examples shown in FIGS. 22 through 25 are intended to be exemplary and are not all possible combinations of how the slide valve 1110 could be constructed. For example, the relative position of the reservoir conduit 1124 and the outlet conduit 1128 can be juxtaposed linearly.

Figure 26:
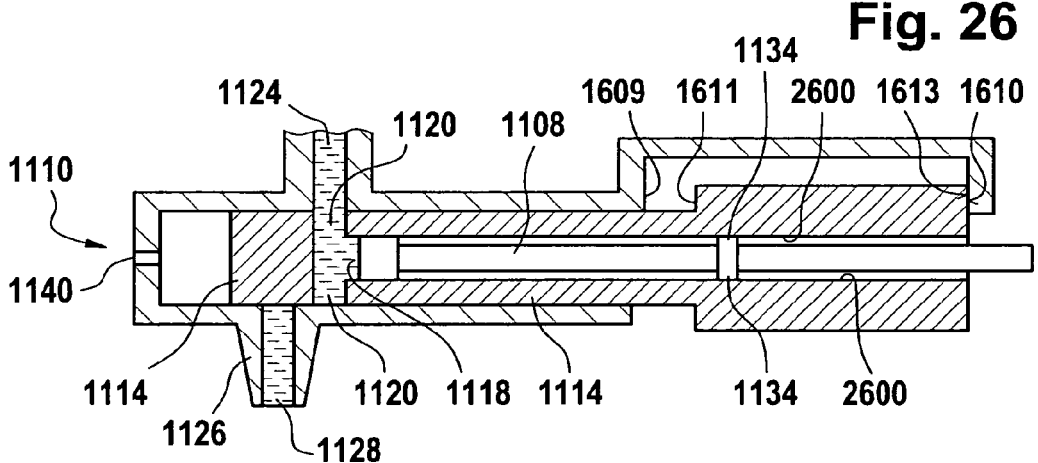
FIG. 26 illustrates an alternative slide valve design according to an embodiment of the present disclosure.
Figure 27:
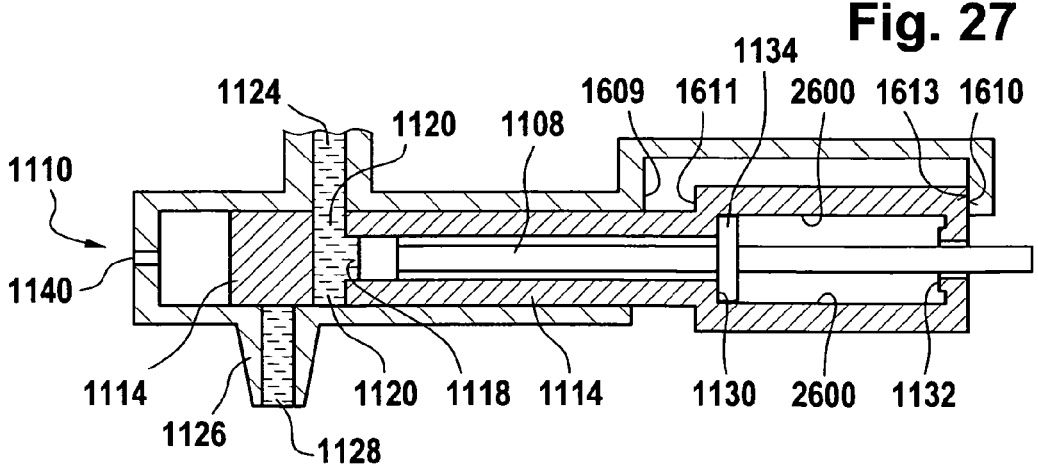
FIG. 27 illustrates an alternative slide valve design according to an embodiment of the present disclosure.

FIGS. 26 and 27 illustrate how the friction between the plunger 1108 and the piston 1114 may be increased. In FIG. 26, the slide valve 1110 is shown as having a vent 1110 as is shown in FIG. 11. The slide valve 1110 can further comprise a reservoir mechanical stop 1610 and an outlet mechanical stop 1609 for contacting the piston 1114. As described previously, these mechanical stops 1609, 1610 can serve to align the pumping chamber conduit 1120 with the reservoir conduit 1124 and the outlet conduit 1128. The plunger 1108 is shown as having the mechanical extensions 1134. However, in the embodiment shown in FIG. 26, there can be no first plunger mechanical stops 1130 or second plunger mechanical stops 1132 as has been previously shown. The mechanical extensions 1134 can contact a surface 2600 within the piston 1114. The contacting mechanical extension 1134 and the surface 2600 can increase the friction between the plunger 1108 and the piston 1114. This can enable the piston 1114 to be actuated by motion of the plunger 1108. As there are no plunger mechanical stops, the movement of the plunger 1108 can be controlled by a linear actuator.

FIG. 18 shows an embodiment of a slide valve 1110 similar to that shown in FIG. 26. The embodiment shown in FIG. 27 is similar to that shown in FIG. 26 except with the addition of a first plunger mechanical stop 1130 and a second plunger mechanical stop 1132 for limiting the travel of the plunger 1108 relative to the piston 1114. Mechanical extensions 1134 can still contact a surface 2600 which can increase the friction between the plunger 1108 and the piston 1114. This can enable the piston 1114 to be actuated by the plunger 1108.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A cartridge for dispensing fluid, the cartridge comprising:
    a valve, wherein the valve comprises a pumping chamber for pumping the fluid, wherein the valve positions a pumping chamber conduit and wherein the pumping chamber conduit is connected with the pumping chamber;
    a plunger for changing the volume of the pumping chamber;
    a reservoir conduit for connecting the reservoir with the valve, wherein the valve positions the pumping chamber conduit to connect with the reservoir conduit; and
    an outlet conduit for dispensing the fluid, wherein the valve rotates the pumping chamber conduit to connect with the outlet conduit, wherein the valve is a rotary valve that rotates the pumping chamber conduit to connect with the reservoir conduit and the outlet conduit, and wherein the rotary valve and the plunger actuated independently.

2. The cartridge according to claim 1, further comprises,
    a return conduit connected to the reservoir that returns fluid to a second portion of the reservoir, wherein the pumping chamber conduit receives fluid from a first portion of the reservoir, and wherein the rotary valve rotates the pumping chamber conduit to connect to the return conduit.

3. The cartridge according to claim 1, further comprises,
    a secondary reservoir; and
    a secondary reservoir conduit, wherein the rotary valve rotates the pumping chamber conduit to connect to the secondary reservoir conduit.

4. The cartridge according to claim 3, further comprises,
    a connecting conduit, wherein the connecting conduit transports fluid between the secondary reservoir and the reservoir.

5. The cartridge according to claim 4, further comprises,
    a membrane blocking the connecting conduit, wherein the membrane is permeable to the fluid.

6. The cartridge according to claim 4, wherein the secondary reservoir comprises a bubble guiding structure.

7. The cartridge according to claim 4, wherein the secondary reservoir comprises a vent, wherein the vent is sealed with a filter, wherein the filter is permeable to air, and wherein the filter seals the fluid in the cartridge.

8. The cartridge according to claim 1, wherein the fluid comprises any one of the following: magnetic beads, latex beads, a dispersion, nanoparticles, a blood grouping reagent, an immune reagent, an antibody, an enzyme, a recombinant protein, a virus isolate, a virus, a biological reagent, solvent, diluent, a protein, a salt, a detergent, a nucleic acid, an acid, a base, and combinations thereof.

9. The cartridge according to claim 1, further comprises,
    a sensor for metering fluid dispensed by the outlet nozzle.

10. The cartridge according to claim 1, further comprises,
    a coupling assembly for attaching the rotary valve and the plunger to an actuator assembly.

11. The cartridge according to claim 1, wherein the rotary valve comprises a cylindrical portion, wherein the pumping chamber is a cavity within the rotary valve, wherein the pumping chamber is formed by the cavity and the plunger, wherein the cartridge comprises a cartridge body with a cylindrical space for receiving the cylindrical portion, and wherein the rotary valve rotates within the cylindrical space.

12. An automatic analyzer for analyzing a biological sample and for holding a cartridge for dispensing fluid, wherein the cartridge comprises a valve, wherein the valve comprises a pumping chamber for pumping the fluid, wherein the pumping chamber is a cavity within the valve, wherein the valve positions a pumping chamber conduit, wherein the pumping chamber conduit is permanently connected with the pumping chamber; a plunger for changing the volume of the pumping chamber, wherein the pumping chamber is formed by the cavity and the plunger; a reservoir conduit for connecting a reservoir with the valve, wherein the valve positions the pumping chamber conduit to connect with the reservoir conduit; and an outlet conduit for dispensing the fluid, wherein the valve further positions the pumping chamber conduit to connect with the outlet conduit, wherein the valve is a rotary valve that rotates a pumping chamber conduit to connect with the reservoir conduit and the outlet conduit, wherein the rotary valve and the plunger actuated independently; the automatic analyzer comprises:

an actuator assembly for actuation of the plunger and of the valve; and
  a controller for controlling the operation of the actuator assembly.

13. The automatic analyzer according to claim 12, wherein the automatic analyzer holds a cartridge for dispensing fluid, wherein the cartridge comprises a valve, wherein the valve comprises a pumping chamber for pumping the fluid, wherein the pumping chamber is a cavity within the valve, wherein the valve positions a pumping chamber conduit, wherein the pumping chamber conduit is permanently connected with the pumping chamber; a plunger for changing the volume of the pumping chamber, wherein the pumping chamber is formed by the cavity and the plunger; a reservoir conduit for connecting a reservoir with the valve, wherein the valve positions the pumping chamber conduit to connect with the reservoir conduit; and an outlet conduit for dispensing the fluid, wherein the valve further positions the pumping chamber conduit to connect with the outlet conduit, wherein the valve is a rotary valve, wherein the rotary valve rotates the pumping chamber conduit, wherein the rotary valve and the plunger actuated independently, wherein the rotary valve rotates the pumping chamber conduit to connect with the reservoir conduit and the outlet conduit, and wherein the actuator assembly is operable for separate linear actuation of the plunger and for rotational actuation of the rotary valve.

14. The automatic analyzer according to claim 13, wherein the controller controls the actuator assembly to rotate the pumping chamber conduit to connect with the reservoir conduit by rotating the rotary valve, controls the actuator assembly to fill the pumping chamber by increasing the volume of the pumping chamber with the plunger, controls the actuator assembly to rotate the pumping chamber conduit to connect with the outlet conduit by rotating the rotary valve, and controls the actuator assembly to pump the fluid through the outlet conduit by decreasing the volume of the pumping chamber with the plunger.

15. The automatic analyzer according to claim 13, wherein the controller controls the actuator assembly to retrieve the fluid from the outlet conduit by increasing the volume of the pumping chamber with the plunger.

16. The automatic analyzer according to claim 13, wherein the controller controls the actuator assembly to rotate the pumping chamber conduit to connect with the reservoir conduit by rotating the rotary valve and controls the actuator assembly to return the fluid to the reservoir by decreasing the volume of the pumping chamber with the plunger.

17. The automatic analyzer according to claim 13, wherein the controller controls the actuator assembly to rotate the pumping chamber conduit to connect with the reservoir conduit by rotating the rotary valve, and controls the actuator assembly to mix the fluid in the reservoir by repeatedly increasing and decreasing the volume of the pumping chamber with the plunger.

18. The automatic analyzer according to claim 13, wherein the cartridge comprises an outlet nozzle, wherein the automatic analyzer further comprises a meniscus detector for detecting a meniscus of the fluid, and wherein the controller controls the actuator to force fluid through the outlet nozzle, detects the meniscus using the meniscus detector, and controls the actuator to halt the forcing of fluid through the outlet when the meniscus is in a predetermined location.

19. The automatic analyzer according to claim 13, wherein the automatic analyzer holds multiple cartridges, wherein the cartridge is one of the multiple cartridges.

20. A method of operating a cartridge for dispensing fluid, wherein the cartridge comprises a valve, wherein the valve comprises a pumping chamber for pumping the fluid, wherein the pumping chamber is a cavity within the valve, wherein the valve positions a pumping chamber conduit, wherein the pumping chamber conduit is permanently connected with the pumping chamber; a plunger for changing the volume of the pumping chamber, wherein the pumping chamber is formed by the cavity and the plunger; a reservoir conduit for connecting a reservoir with the valve, wherein the valve positions the pumping chamber conduit to connect with the reservoir conduit; and an outlet conduit for dispensing the fluid, wherein the valve further positions the pumping chamber conduit to connect with the outlet conduit, and wherein the valve is a rotary valve, wherein the rotary valve rotates the pumping chamber conduit, wherein the rotary valve and the plunger actuated independently, wherein the rotary valve rotates the pumping chamber conduit to connect with the reservoir conduit and the outlet conduit, wherein the rotary valve and the plunger actuated independently the method comprising:

rotating the rotary valve to rotate the pumping chamber conduit to connect with the reservoir conduit;
  increasing the volume of the pumping chamber with the plunger to fill the pumping chamber;
  rotating the rotary valve to rotate the pumping chamber conduit to connect with the outlet conduit; and
  decreasing the volume of the pumping chamber with the plunger to pump the fluid through the outlet conduit.

* * * * *